US009074246B2

(12) United States Patent
Ju

(10) Patent No.: US 9,074,246 B2
(45) Date of Patent: Jul. 7, 2015

(54) SELF-FOLDING AMPLIFICATION OF TARGET NUCLEIC ACID

(75) Inventor: Jingliang Ju, San Diego, CA (US)

(73) Assignee: RD Biosciences, Inc., San Diego, CA (US)

(*) Notice: Subject to any disclaimer, the term of this patent is extended or adjusted under 35 U.S.C. 154(b) by 279 days.

(21) Appl. No.: 13/574,767

(22) PCT Filed: Jan. 25, 2011

(86) PCT No.: PCT/US2011/022326
§ 371 (c)(1),
(2), (4) Date: Oct. 29, 2012

(87) PCT Pub. No.: WO2011/091393
PCT Pub. Date: Jul. 28, 2011

(65) Prior Publication Data
US 2013/0040344 A1    Feb. 14, 2013

Related U.S. Application Data

(60) Provisional application No. 61/297,823, filed on Jan. 25, 2010.

(51) Int. Cl.
| C12Q 1/68 | (2006.01) |
| C12P 19/34 | (2006.01) |
| C12N 15/10 | (2006.01) |
| C12Q 1/70 | (2006.01) |

(52) U.S. Cl.
CPC .......... *C12Q 1/6853* (2013.01); *C12N 15/1096* (2013.01); *C12Q 1/6844* (2013.01); *C12Q 1/6865* (2013.01); *C12Q 1/707* (2013.01)

(58) Field of Classification Search
None
See application file for complete search history.

(56) References Cited

U.S. PATENT DOCUMENTS

| 4,683,195 | A | | 7/1987 | Mullis et al. |
| 4,683,202 | A | | 7/1987 | Mullis |
| 4,786,600 | A | | 11/1988 | Kramer et al. |
| 4,800,159 | A | | 1/1989 | Mullis et al. |
| 4,868,105 | A | | 9/1989 | Urdea et al. |
| 5,124,246 | A | | 6/1992 | Urdea et al. |
| 5,130,238 | A | | 7/1992 | Malek et al. |
| 5,399,491 | A | | 3/1995 | Kacian et al. |
| 5,422,252 | A | | 6/1995 | Walker et al. |
| 5,437,990 | A | * | 8/1995 | Burg et al. .................... 435/91.2 |
| 5,516,663 | A | | 5/1996 | Backman et al. |
| 5,545,522 | A | * | 8/1996 | Van Gelder et al. ............ 506/26 |
| 5,547,861 | A | | 8/1996 | Nadeau et al. |
| 5,554,516 | A | | 9/1996 | Kacian et al. |
| 5,679,512 | A | | 10/1997 | Laney et al. |
| 5,714,320 | A | | 2/1998 | Kool |
| 5,834,252 | A | | 11/1998 | Stemmer et al. |
| 5,866,336 | A | | 2/1999 | Nazarenko et al. |
| 6,251,639 | B1 | | 6/2001 | Kurn |
| 7,294,461 | B2 | | 11/2007 | Kurn |
| 7,579,154 | B2 | * | 8/2009 | Chun ........................... 435/6.12 |
| 2005/0064432 | A1 | * | 3/2005 | Huang et al. ...................... 435/6 |
| 2005/0147975 | A1 | | 7/2005 | Schembri et al. |
| 2006/0046265 | A1 | | 3/2006 | Becker et al. |
| 2009/0220969 | A1 | | 9/2009 | Chiang et al. |
| 2009/0325813 | A1 | | 12/2009 | Wang et al. |
| 2010/0092963 | A1 | * | 4/2010 | Ju ..................................... 435/6 |

FOREIGN PATENT DOCUMENTS

| EP | 0 320 308 B1 | 6/1989 |
| WO | WO-88/10315 A1 | 12/1988 |
| WO | WO-00/70095 A2 | 11/2000 |
| WO | WO-00/70095 A3 | 11/2000 |
| WO | WO-02/00938 A2 | 1/2002 |
| WO | WO-02/00938 A3 | 1/2002 |
| WO | WO-02/00938 A9 | 1/2002 |
| WO | WO-2006/081222 A2 | 8/2006 |
| WO | WO-2006/081222 A3 | 8/2006 |
| WO | WO-2008/080029 A2 | 7/2008 |
| WO | WO-2008/080029 A3 | 7/2008 |
| WO | WO-2008/080029 A9 | 7/2008 |
| WO | WO-2008/085652 A1 | 7/2008 |
| WO | WO 2008080029 A2 * | 7/2008 |
| WO | WO-2008/108843 A2 | 9/2008 |
| WO | WO-2008/108843 A3 | 9/2008 |

OTHER PUBLICATIONS

Grivna, S.T. et al. (2006). "A Novel Class of Small RNAs in Mouse Spermatogenic Cells," *Genes Dev.* 20:1709-1714.
Hamilton, A.J. et al. (Oct. 29, 1999). "A Species of Small Antisense RNA in Posttranscriptional Gene Silencing in Plants," *Science* 286(5441):950-952.
Hammond, S.M. et al. (Mar. 16, 2000). "An RNA-Directed Nuclease Mediates Post-Transcriptional Gene Silencing in *Drosophila* cells," *Nature* 404:293-296.
Kowh, D.Y. (Feb. 1, 1989). "Transcription-Based Amplification System and Detection of Amplified Human Immunodeficiency Virus Type 1 With a Bead-Based Sandwich Hybridzation Format," *Proc. Natl. Acad. Sci. USA* 86(4):1173-1177.
Lee, R.C. et al. (Dec. 3, 1993). "The *C. Elegans* Heterochronic Gene *lin-4* Encodes Small RNAs With Antisense Complementarity to *lin-14*," *Cell* 75(5):843-854.

(Continued)

*Primary Examiner* — Prabha Chunduru
(74) *Attorney, Agent, or Firm* — Morrison & Foerster LLP

(57) ABSTRACT

The application relates generally to methods useful for the selective amplification of one or more target nucleic acid or fragments thereof, as well as compositions and kits comprising said amplification reaction mixtures. More specifically, the application relates to a composite primer that comprises a 5' promoter portion and a 3' target-recognition portion which is complementary to the 3' end portion of a target polynucleotide sequence; and optionally, a means for identifying the 5' end portion of the target polynucleotide sequence. The amplification reaction mixture comprises at least one handle-stem-loop structure which comprises a 5' single-stranded handle comprising the promoter portion and a double-stranded stem comprising at least one pair of self-folding segments hybridized to each other, and optionally, a single-stranded loop comprising the sequence between the pair of self-folding segments.

20 Claims, 11 Drawing Sheets

(56) References Cited

OTHER PUBLICATIONS

Figure 1:
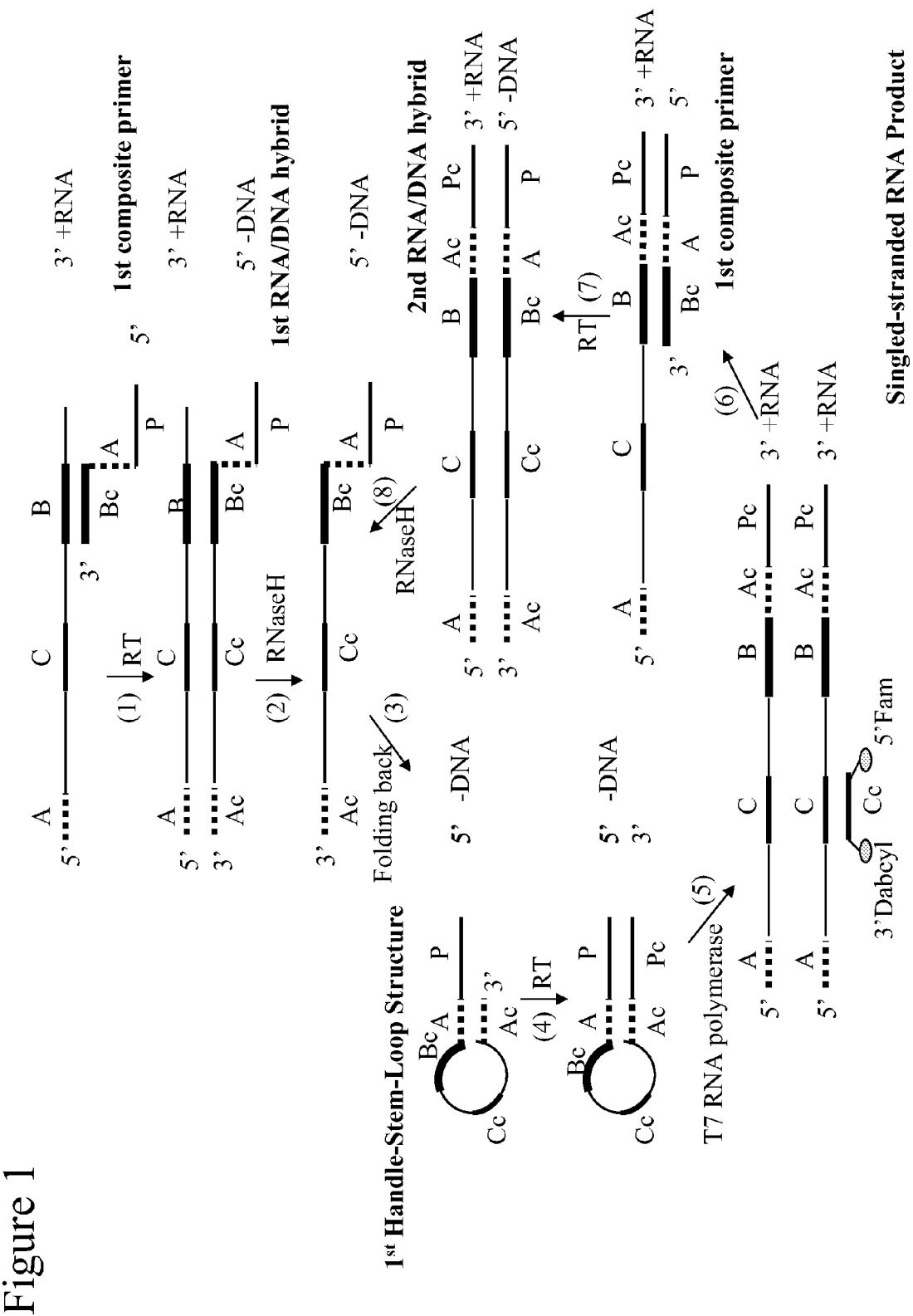

Reinhart, B.J. et al. (Feb. 24, 2000). "The 21-Nucleotide *let-7* RNA Regulates Developmental Timing in *Caenorhabditis elegans*," *Nature* 403(6772):901-906.

Reinhart, B.J. et al. (Sep. 13, 2002, e-pub. Aug. 22, 2002). "Small RNAs Correspond to Centromere Heterochromatic Repeats," *Science* 297:1831.

Volpe, T.A. et al. (Sep. 13, 2002, e-pub. Aug. 22, 2002). "Regulation of Heterochromatic Silencing and Histone H3 Lysine-9 Methylation by RNAi," *Science* 297:1833-1837.

International Search Report mailed on Mar. 11, 2011, for PCT Application No. PCT/US2011/022326, filed on Jan. 25, 2011, 5 pages.

Written Opinion mailed on Mar. 11, 2011, for PCT Application No. PCT/US2011/022326, filed on Jan. 25, 2011, 5 pages.

\* cited by examiner

SELF-FOLDING AMPLIFICATION OF TARGET NUCLEIC ACID

This application is a U.S. national stage application of PCT application serial No. PCT/US2011/022326, having an international filing date of Jan. 25, 2011, which claims the benefit of priority of provisional application Ser. No. 61/297,823, filed Jan. 25, 2010, each of which the entire contents are incorporated herein by reference.

Incorporated herein by reference is the Sequence Listing being concurrently submitted via EFS-Web as an ASCII text file named 12649_005_999 Sequence_Listing.TXT, created Jul. 23, 2012, and being 1,696 bytes in size.

1. FIELD OF THE INVENTION

The application relates generally to kits and methods useful for the selective amplification of one or more target polynucleotide sequences (often within a longer polynucleotide template) as well as amplification reaction mixtures resulting from the methods. Specifically, the kit comprises a composite primer for initiating primer extension over the length of the target sequence to make a single-stranded DNA product and optionally, a means for producing a defined 3' end for the single-stranded DNA product of the primer extension. The composite primer comprises a 5' promoter portion and a 3' target-recognition portion which is complementary to the 3' end portion of the target sequence. The means for producing a defined 3' end for the single-stranded DNA product could be a restriction enzyme (or other enzymes) that cuts or nicks immediately upstream of the 5' end of the target sequence or a nucleotide sequence (e.g., a blocking oligonucleotide or template switching oligonucleotide (TSO)) which hybridizes immediately upstream of the 5' end of the target sequence. The 3' end portion of the single-stranded DNA product hybridizes to a complementary sequence in the same single-stranded DNA product by self-folding, and forms a handle-stem-loop structure which comprises (i) a 5' single-stranded handle comprising the promoter portion, (ii) a double-stranded stem comprising the 3' end portion of the single-stranded DNA product hybridized to its complementary sequence, and optionally, (iii) a single-stranded loop comprising the sequence between the hybridized sequences. The 3' end of the handle-stem-loop structure is further extended over the 5' single-stranded handle to form a double stranded promoter which in turn initiates transcription of the target sequence. The amplification reaction mixtures comprise amplified ribonucleotide target sequence, the composite primer, and the self-folding single-stranded DNA product.

2. BACKGROUND

Nucleic acid amplification techniques are powerful tools in making more copies of a nucleic acid that is few in number. Amplification techniques have widespread application including, for example, diagnostics, drug development, forensic investigations, environmental analysis, and food testing.

There are a number of well known methods for amplifying nucleic acid sequences in vitro including, for example, polymerase chain reaction (PCR), ligase chain reaction (LCR), replicase-mediated amplification, strand-displacement amplification (SDA), "rolling circle" types of amplification, and various nucleic acid sequence-based amplification (NASBA) and transcription-medicated amplification (TMA) methods. These methods use different techniques to make amplified sequences, which usually are detected by using a variety of methods. PCR amplification uses a DNA polymerase, oligonucleotide primers, and thermal cycling to synthesize multiple copies of both strands of a double-stranded DNA (dsDNA) or dsDNA made from a cDNA (see, e.g., U.S. Pat. Nos. 4,683,195, 4,683,202, and 4,800,159 to Mullis et al.). LCR amplification uses an excess of two complementary pairs of single-stranded probes that hybridize to contiguous target sequences and are ligated to form fused probes complementary to the original target, which allows the fused probes to serve as a template for further fusions in multiple cycles of hybridization, ligation, and denaturation (see, e.g., U.S. Pat. No. 5,516,663 and EP 0320308 B1 to Backman et al.). Replicase-mediated amplification uses a self-replicating RNA sequence attached to the analyte sequence and a replicase, such as Qβ-replicase, to synthesize copies of the self-replicating sequence specific for the chosen replicase, such as a Qβ viral sequence (see, e.g., U.S. Pat. No. 4,786,600 to Kramer et al.). The amplified sequence is detected as a substitute or reporter molecule for the analyte sequence. SDA amplification uses a primer that contains a recognition site for a restriction endonuclease which allows the endonuclease to nick one strand of a hemimodified dsDNA that includes the target sequence, followed by a series of primer extension and strand displacement steps (see, e.g., U.S. Pat. No. 5,422,252A to Walker et al., and U.S. Pat. No. 5,547,861 to Nadeau et al.). "Rolling circle" types of amplification rely on a circular or concatenated nucleic acid structure that serves as a template used to enzymatically replicate multiple single-stranded copies from the template (see, e.g., U.S. Pat. No. 5,714,320 to Kool, and U.S. Pat. No. 5,834,252 to Stemmer et al.). TMA amplification refers to methods that amplify a sequence by producing multiple transcripts from a nucleic acid template. Such methods generally use one or more oligonucleotides, of which one provides a promoter sequence, and enzymes with RNA polymerase and DNA polymerase activities to make a functional promoter sequence near the target sequence and then transcribe the target sequence from the promoter (see, e.g., U.S. Pat. Nos. 5,399,491 and 5,554,516 to Kacian et al., U.S. Pat. No. 5,437,990 to Burg et al., WO 88/010315 to Gingeras et al., U.S. Pat. No. 5,130,238 to Malek et al., U.S. Pat. Nos. 4,868,105 and 5,124,246 to Urdea et al., and US 2006-0046265 A1 to Becker et al.). Nucleic acid amplification methods may amplify a specific target sequence (e.g., a gene sequence), a group of related target sequences, or a surrogate sequence, which may be referred to as a tag or reporter sequence that is amplified and detected in place of the analyte sequence. The surrogate sequence is only amplified if the analyte target sequence is present at some point during the reaction.

The above described technologies often require the use of two or more primers for target amplification. Design and optimization of the primers for each target is required. This is a costly, time-consuming and often challenging and difficult process, especially in multiplex assays for amplifying two or more different target sequences where cross-reaction of primer pairs could be a serious challenge to reliability of the assays. It is also extremely difficult (if not impossible) to design and optimize two primers for amplification of small targets (such as microRNAs, which contains only 18 to 25 nucleotides).

The present invention describes amplification methods using a single composite primer which overcomes the difficulties described above.

3. SUMMARY OF THE INVENTION

A first aspect of the invention relates to methods for the selective amplification, and optionally, the detection, of one or more target polynucleotide sequences (used interchangeably with "target sequence"). In some embodiments, the target sequence is within a longer polynucleotide template.

Specifically, the methods are useful for the selective amplification, and optionally, the detection, of one or more target sequences in a transcription-mediated amplification (TMA) system. More specifically, the method uses a composite primer for initiating primer extension over the length of the target sequence to make a single-stranded DNA product, and in those situations where the target sequence is within a longer polynucleotide template, the method additionally uses a means for producing a defined 3' end for the single-stranded DNA product of the primer extension. The composite primer comprises a 5' promoter portion and a 3' target-recognition portion which is complementary to the 3' end portion of the target sequence. The means for producing a defined 3' end for the single-stranded DNA product of the primer extension works by identifying the 5' end of the target sequence: in one embodiment, an enzyme (e.g., a restriction enzyme) is used to cut or nick immediately upstream of the 5' end of the target sequence; in another embodiment, a nucleotide sequence (e.g., a blocking oligonucleotide or template switching oligonucleotide (TSO)) is used to hybridize immediately upstream of the 5' end of the target sequence. The 3' end portion of the single-stranded DNA product hybridizes to a complementary sequence in the same single-stranded DNA product by self-folding, and forms a handle-stem-loop structure which comprises (i) a 5' single-stranded handle comprising the promoter portion, (ii) a double-stranded stem comprising the 3' end portion of the single-stranded DNA product hybridized to its complementary sequence, and optionally, (iii) a single-stranded loop comprising the sequence between the hybridized sequences. The 3' end of the handle-stem-loop structure is further extended over the 5' single-stranded handle to form a double stranded promoter which in turn initiates transcription of the target sequence.

In certain embodiments, the 5' end of the target sequence corresponds to a portion of the composite primer that does not overlap with the promoter portion or the target-recognition portion. In certain other embodiments, the 5' end of the target sequence is complementary to a portion of the composite primer, such as the target-recognition portion, and does not overlap with the promoter portion. In certain other embodiments, the 5' end of the target sequence is complementary to a portion of the target sequence that is not complementary to the target-recognition portion of the composite primer. In some of those embodiments where the target sequence is within a longer polynucleotide template, the 5' end of the target sequence is introduced during primer extension, for example, by use of a template switching oligonucleotide (TSO) that hybridizes to a region of the polynucleotide template intended to be immediately upstream of the 5' end of the target sequence.

Typically, a method of the invention relates to the selective amplification of at least one target polynucleotide sequence (T), said method comprising the steps of:
 (a) hybridizing the target polynucleotide sequence with a first composite primer, said first composite primer comprising a 5' promoter portion (P) and a 3' target-recognition portion which is complementary to the 3' end portion of the target polynucleotide sequence;
 (b) identifying the 5' end portion of the target polynucleotide sequence;
 (c) extending the 3' end of the first composite primer and generating a first single-stranded DNA template comprising the promoter portion (P) and the complementary sequence of the target polynucleotide sequence (Tc), said first single-stranded DNA template comprising a first pair of self-folding segments that are complementary to each other, wherein the promoter portion (P) is at the 5' end of the first single-stranded DNA template and one of the self-folding segments is at the 3' end of the first single-stranded DNA template;
 (d) allowing the first single-stranded DNA template to self-fold and form a first handle-stem-loop structure, which comprises a 5' single-stranded handle comprising the promoter portion (P) and a double-stranded stem comprising the first pair of self-folding segments hybridized to each other;
 (e) extending the 3' end of the first handle-stem-loop structure to generate a double-stranded promoter comprising the promoter portion (P) and its complementary sequence (Pc) hybridized to each other; and
 (f) initiating transcription from the double-stranded promoter to generate multiple copies of a single-stranded RNA product comprising the target polynucleotide sequence (T).

In some embodiments, the pair of self-folding segments are separated from each other. In some embodiments, the pair of self-folding segments are adjacent or next to each other.

In some embodiments, the handle-stem-loop structure further comprises a single-stranded loop comprising the sequence between the pair of self-folding segments. The number of bases in the sequence between the pair of self-folding segments can be anywhere between 0 and 1000, preferably between 1 and 200, and more preferably between 5 and 100.

In some embodiments, the single-stranded RNA product comprises at its 3' end the complementary sequence of the promoter portion (Pc).

In certain methods, the target polynucleotide sequence is RNA, and step (c) comprises extending the 3' end of the first composite primer to generate a first RNA/DNA hybrid and removing the RNA portion of the first RNA/DNA hybrid to generate the first single-stranded DNA template.

In certain methods, the target polynucleotide sequence is DNA, and the method comprises a denaturing step before step (a), and step (c) comprises extending the 3' end of the composite primer to generate a first DNA/DNA hybrid and denaturing the first DNA/DNA hybrid to generate the first single-stranded DNA template.

In certain embodiments, the target polynucleotide sequence is within a longer polynucleotide template, and step (b) comprises identifying the 5' end of the target polynucleotide sequence by using an enzyme to cleave at a region of the polynucleotide template immediately upstream of the 5' end of the target polynucleotide sequence.

In certain embodiments, the target polynucleotide sequence is within a longer polynucleotide template, and step (b) comprises identifying the 5' end of the target polynucleotide sequence by hybridizing a nucleotide sequence such as a blocking oligonucleotide or a template switching oligonucleotide (TSO) to a region of the polynucleotide template immediately upstream of the 5' end of the target polynucleotide sequence. In a specific embodiment, step (b) comprises identifying the 5' end of the target polynucleotide sequence by hybridizing a blocking oligonucleotide to a region of the polynucleotide template immediately upstream of the 5' end of the target polynucleotide sequence, wherein said blocking oligonucleotide block extension of the composite primer in step (c). In another specific embodiment, step (b) comprises identifying the 5' end of the target polynucleotide sequence by hybridizing a TSO to a region of the polynucleotide template immediately upstream of the 5' end of the target polynucleotide sequence, and wherein step (c) comprises extending the 3' end of the composite primer over a portion of said TSO. Preferably, the blocking oligonucleotide or TSO is 6 to 100 bases in length. Blocking oligonucleotide and TSO useful in the methods can be those well known in the art. For example, the blocking oligonucleotide or TSO can comprise modified bases to enhance hybridization affinity, such as locked nucleic acid (LNA), 2'-O-methyl (2'-OMe) bases, etc.

In some of those embodiments involving use of a blocking oligonucleotide, the first composite primer further comprises, between the promoter portion (P) and the 3' target-recognition portion, a segment corresponding to the 5' end portion of the target polynucleotide sequence, wherein this segment and its complementary sequence form said first pair of self-folding segments, the method further comprising the following steps after step (f):

(g) hybridizing the single-stranded RNA product with the first composite primer (−) and extending the 3' end of the first composite primer to generate a second RNA/DNA hybrid;

(h) removing the RNA portion of the second RNA/DNA hybrid to generate the first single-stranded DNA template; and continuing steps (d), (e) and (f).

In some of those embodiments involving use of a blocking oligonucleotide, the 3' target-recognition portion of the first composite primer comprises a segment corresponding to the 5' end portion of the target polynucleotide sequence, wherein this segment and its complementary sequence form said first pair of self-folding segments, the method further comprising the following steps after step (f):

(g) hybridizing the single-stranded RNA product with the first composite primer and extending the 3' end of the first composite primer to generate a second RNA/DNA hybrid;

(h) removing the RNA portion of the second RNA/DNA hybrid to generate a second single-stranded DNA template comprising the promoter portion (P) and the complementary sequence of the target polynucleotide sequence (Tc), said second single-stranded DNA template comprising a second pair of self-folding segments that are complementary to each other, wherein the promoter portion (P) is at the 5' end of the second single-stranded DNA template and one of the second pair of self-folding segments is at the 3' end of the second single-stranded DNA template;

(i) allowing the second single-stranded DNA template to self-fold and form a second handle-stem-loop structure, which comprises a 5' single-stranded handle comprising the promoter portion (P) and a double-stranded stem comprising the second pair of self-folding segments hybridized to each other;

(j) extending the 3' end of the second handle-stem-loop structure to generate a double-stranded promoter comprising the promoter portion (P) and its complementary sequence (Pc) hybridized to each other; and (k) initiating transcription from the double-stranded promoter to generate multiple copies of the single-stranded RNA product.

In some of those embodiments involving use of a blocking oligonucleotide, the first pair of self-folding segments comprise a segment corresponding to the 5' end portion of the target polynucleotide sequence and its complementary sequence located at a separate portion of the target polynucleotide sequence, the method further comprising the following steps after step (f):

(g) hybridizing the single-stranded RNA product with the first composite primer and extending the 3' end of the first composite primer to generate a second RNA/DNA hybrid;

(h) removing the RNA portion of the second RNA/DNA hybrid to generate a second single-stranded DNA template comprising the promoter portion (P) and the complementary sequence of the target polynucleotide sequence (Tc), said second single-stranded DNA template comprising a second pair of self-folding segments that are complementary to each other, wherein the promoter portion (P) is at the 5' end of the second single-stranded DNA template and one of the second pair of self-folding segments is at the 3' end of the second single-stranded DNA template;

(i) allowing the second single-stranded DNA template to self-fold and form a second handle-stem-loop structure, which comprises a 5' single-stranded handle comprising the promoter portion (P) and a double-stranded stem comprising the second pair of self-folding segments hybridized to each other;

(j) extending the 3' end of the second handle-stem-loop structure to generate a double-stranded promoter comprising the promoter portion (P) and its complementary sequence (Pc) hybridized to each other; and (k) initiating transcription from the double-stranded promoter to generate multiple copies of the single-stranded RNA product.

In some of those embodiments involving use of a TSO, the first composite primer further comprises, from 5' to 3' and between the promoter portion (P) and the 3' target-recognition portion, a universal portion (U) that is not present in the target polynucleotide sequence or its complementary sequence, and the template switching oligonucleotide (TSO) comprising, from 5' to 3', the universal portion (U) and a portion complementary to the region of the polynucleotide template immediately upstream of the 5' end of the target polynucleotide sequence, wherein the first pair of self-folding segments comprise the universal portion (U) and its complementary sequence, the method further comprising the following steps after step (f):

(g) hybridizing the single-stranded RNA product with the first composite primer or a second composite primer and extending the 3' end of the second composite primer to generate a second RNA/DNA hybrid, wherein the second composite primer comprises the 5' promoter portion (P) and the universal portion (U);

(h) removing the RNA portion of the second RNA/DNA hybrid to generate the first single-stranded DNA template; and continuing steps (d), (e) and (f). Alternatively, a second composite primer comprising the 5' promoter portion (P) and the universal portion (U) can be used in step (g). In a preferred embodiment, the second composite primer consists of, or more preferably, consists essentially of, from 5' to 3', the promoter portion (P) and the universal portion (U).

Any of the above described methods, either alone or in various combinations, can be used in the selective, and preferably, simultaneous, amplification of multiple target polynucleotide sequences. For example, the method can use a different first composite primer for each target polynucleotide sequence, wherein each first composite primer further comprises, from 5' to 3' and between the promoter portion (P) and the 3' target-recognition portion, a universal portion (U) that is not present in the target polynucleotide sequence or its complementary sequence, and a segment corresponding to the 5' end portion of the target polynucleotide sequence, wherein this segment and its complementary sequence form said first pair of self-folding segments, the method further comprising the following steps after step (f):

(g) hybridizing the single-stranded RNA product with the first composite primer or a second composite primer and extending the 3' end of the second composite primer to generate a second RNA/DNA hybrid, wherein the second composite primer comprises the 5' promoter portion (P) and the universal portion (U);

(h) removing the RNA portion of the second RNA/DNA hybrid to generate a second single-stranded DNA template comprising the promoter portion (P), the universal portion (U), and the complementary sequence of the target polynucleotide sequence (Tc), said second single-stranded DNA template comprises a second pair of self-folding segments that are complementary to and separated from each other, wherein the promoter portion (P) is at the 5' end of the second single-stranded DNA template and one of the second pair of self-folding segments is at the 3' end of the second single-stranded DNA template;

(i) allowing the second single-stranded DNA template to self-fold and form a second handle-stem-loop structure which comprises a 5' single-stranded handle comprising the promoter portion (P), a double-stranded stem comprising the second pair of self-folding segments hybridized to each other, and a single-stranded loop comprising the sequence between the second pair of self-folding segments;

(j) extending the 3' end of the second handle-stem-loop structure to generate a double-stranded promoter comprising the promoter portion (P) and its complementary sequence (Pc) hybridized to each other; and (k) initiating transcription from the double-stranded promoter to generate multiple copies of the single-stranded RNA product.

Alternatively, a second composite primer comprising the 5' promoter portion (P) and the universal portion (U) can be used in step (g). In a preferred embodiment, the second composite primer consists of, or more preferably, consists essentially of, from 5' to 3', the promoter portion (P) and the universal portion (U).

Optionally, the above described methods can further comprise a detection step comprising a means for detecting the single-stranded RNA product. In one aspect, the detection means is selected from the group consisting of hybridization protection assay (HPA), molecular beacon, TaqMan probe, fluorescence resonance energy transfer (FRET) probe, induced FRET (iFRET) probes, minor grove binder (MGB) probe, molecular torch, and hybridization switch probe. Preferably, the detection means comprises a sequence complementary to a portion of the target polynucleotide sequence, and said sequence is not found in the composite primer or its complementary sequence.

In certain embodiments, the target polynucleotide sequence is a positive-sense (or plus (+)-strand), and the composite primer(s) is negative-sense (or minus (−)-strand), and the single-stranded RNA product is positive-sense (+). In certain other embodiments, the target polynucleotide sequence is negative (−)-sense, and the composite primer(s) is positive (+)-sense, and the single-stranded RNA product is negative (−)-sense.

A second aspect of the invention relates to kits useful for the selective amplification, and optionally, the detection, of one or more target polynucleotide sequences (used interchangeably with "target sequence").

In some embodiments, the target sequence is not within a longer polynucleotide sequence (e.g., microRNA, siRNA, rasiRNA, piRNA, tnc RNA, and smRNA, defined below). In these situations, the kit comprises, for each target sequence, at least one composite primer comprising a 5' promoter portion and a 3' target-recognition portion which is complementary to the 3' end portion of a target sequence. The composite primer is for initiating primer extension over the length of the target sequence to make a single-stranded DNA product.

In some embodiments, the target sequence is within a longer polynucleotide sequence. In these situations, the kit comprises, for each target sequence, at least one composite primer comprising a 5' promoter portion and a 3' target-recognition portion which is complementary to the 3' end portion of a target sequence, and a means for identifying the 5' end portion of the target sequence, and optionally, a detection means. The means is for producing a defined 3' end for the single-stranded DNA product of the primer extension.

In certain embodiments, the composite primer(s), the optional identifying means, and the optional detection means are placed in the same container means of the kit. In certain embodiments, the composite primer(s), the optional identifying means, and the optional detection means are placed in separate container means of the kit.

Optionally, the kits of the invention further comprises an instruction manual describing, for example, the component(s) within each container means, the order of using the one or more container means, etc.

A third aspect of the invention relates to compositions comprising one or more target sequence, one or more composite primer, and one or more amplification reaction product (including, but not limited to, amplified ribonucleotide target sequence, and self-folding single-stranded DNA product). The self-folding single-stranded DNA product includes a handle-stem-loop structure and a stem-loop structure. The handle-stem-loop comprises a (i) a 5' single-stranded handle comprising a promoter portion (P), (ii) a double-stranded stem comprising at least one pair of self-folding segments hybridized to each other, wherein one of the self-folding segment is the 5' end portion of the target polynucleotide sequence or its complementary sequence, and optionally (iii) a single-stranded loop comprising the sequence between the pair of self-folding segments. The stem-loop structure is different from the handle-stem-loop structure in that the 5' single-stranded handle has become double-stranded following primer extension.

3.1 Abbreviations and Terms

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and are described below. The materials, methods, and examples described herein are illustrative only and are not intended to be limiting.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The terms "3' end portion" and "3' end region" generally refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' end portion or region can comprise preferably from about 1 to about 20, more preferably from about 3 to about 18, even more preferably from about 5 to about 15 nucleotides.

The terms "5' end portion" and "5' end region" generally refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' end portion or region can comprise preferably from about 1 to about 20, more preferably from about 3 to about 18, even more preferably from about 5 to about 15 nucleotides.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

The term "amplification" generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "blocking oligonucleotide," "blocking sequence," "blocker sequence," or "blocker," as used interchangeably herein, is a polynucleotide or oligonucleotide that binds, generally with high affinity, to the template nucleic acid at a location 5' to the termination site and effects cessation of DNA replication by DNA polymerase with respect to the template comprising the target sequence. Its 3' end may or may not be blocked for extension by DNA polymerase. Blocking oligonucleotides are generally known in the art. In preferred embodiments, the blocking oligonucleotide comprises a modification in the region which hybridizes to the template, wherein, under a given set of conditions, the blocker binds more tightly to the region as compared to a blocker without the modification. Examples of suitable modifications include, but without limitation, locked nucleic acid (LNA), 2'-O-methyl (2'-OMe) bases, etc., as well as those described in, for example, U.S. Pat. No. 7,294,461 to Kurn.

The term "detection" includes any means of detecting, including direct and indirect detection. For example, "detectably fewer" products may be observed directly or indirectly, and the term indicates any reduction (including no products). Similarly, "detectably more" product means any increase, whether observed directly or indirectly.

"Identifying the 5' end portion of the target polynucleotide sequence," as used herein, refers to locating or generating the 5' end of the target polynucleotide sequence for guiding the termination or template switch of a primer extension process over the target polynucleotide sequence. Means for identifying the 5' end portion of the target polynucleotide sequence include, without limitation, an enzyme (e.g., restriction enzyme) that cuts or nicks a region in the template immediately upstream of the 5' end of the target sequence, and a nucleotide sequence (e.g., a blocking oligonucleotide or template switching oligonucleotide (TSO)) which hybridizes to a region in the template immediately upstream of the 5' end of the target sequence. In certain embodiments, a short target sequence is not within a longer polynucleotide template, and thus, no active step is involved in identifying the 5' end portion of the short target sequence, since the 5' end portion is the natural 5' end portion of the short target sequence, and need not be isolated (e.g., by cutting, cleaving or nicking through enzyme action) or generated (e.g., by blocking oligonucleotide or TSO hybridization prior to the primer extension process). Examples of short RNA targets include, without limitation, microRNA (miRNA: Lee et al. 1993, Cell 75:843-854; Reinhart et al., 2000, Nature 403:901-906), small interfering RNA (siRNA: Hamilton et al. 1999, Science 286:950-952; Hammond et al. Nature 404:293-296), repeat-associated small interfering RNA (rasiRNA: Reinhart and Bartel 2002, Science 297:183; Volpe et al. 2002, Science 297:1833-1837), and PIWI-interacting RNA (piRNA: Grivna et al. 2006, Genes Dev. 20:1709-1714), as described in US 2009-0220969 A1 to Chiang et al.; and tiny non-coding RNA (tnc RNA) and small modulatory RNA (smRNA), as described in US 2009-0325813 A1 to Wang et al.

The term "oligonucleotide" generally refers to short, generally single-stranded, generally synthetic polynucleotides that are generally, but not necessarily, less than about 200 nucleotides in length. Oligonucleotides in the present invention include, for example, the composite primer, the blocking oligonucleotide, and TSO. The terms "oligonucleotide" and "polynucleotide" are not mutually exclusive. The description below for polynucleotides is equally and fully applicable to oligonucleotides.

A "portion" or "region," as used interchangeably herein, of a polynucleotide or oligonucleotide is a contiguous sequence of 2 or more bases. In other embodiments, a portion or region is at least about any of 3, 5, 10, 15, 20, 25 contiguous nucleotides.

The term "promoter sequence" generally refers to a single-stranded DNA sequence region which, in double-stranded form is capable of mediating RNA transcription. In some contexts, "promoter sequence," and "promoter" are used interchangeably. Examples of promoter sequences include, without limitation, sequences that can be recognized by T7, T3, SP6, M13 RNA polymerase, etc.

Reverse transcriptase, also known as RNA-dependent DNA polymerase, is a DNA polymerase enzyme that transcribes single-stranded RNA into double-stranded DNA. Examples of reverse transcriptase include, without limitation, MMLV reverse transcriptase, AMV reverse transcriptase, etc.

A "target polynucleotide sequence" or "target sequence," as used interchangeably herein, is a polynucleotide sequence of interest, for which amplification is desired. The target sequence may be known or not known, in terms of its actual sequence. Generally, a "polynucleotide template" or "template," as used interchangeably herein, is a polynucleotide that contains the target sequence. In some instances, the terms "target sequence," "template," "polynucleotide template," "target nucleic acid," "target polynucleotide," and variations thereof, are used interchangeably herein.

The term "template switch oligonucleotide (TSO)" generally refers to a polynucleotide or an oligonucleotide that comprises a portion (or region) that hybridizes to a template at a location 5' to the termination site of primer extension and that is capable of effecting a template switch in the process of primer extension by a DNA polymerase. TSOs are generally known in the art. "Template switch" refers to a change in template nucleic acid, generally from the target nucleic acid to the unhybridized portion of a TSO, during the course of a single round of primer extension. Examples of TSO include, without limitation, those described in WO 00/070095 to Kurn et al.

The terms "termination polynucleotide sequence" and "termination sequence," as used interchangeably herein, refers to a polynucleotide sequence which effects cessation of DNA replication by DNA polymerase with respect to the template comprising the target sequence. A termination sequence comprises a portion (or region) that generally hybridizes to the template at a location 5' to the termination point (site). Examples of suitable termination polynucleotide sequences (such as blocking oligonucleotides and TSOs) are provided herein.

The terms "termination site" and "termination point," as used interchangeably herein, refer to the site, point or region of the template that is last replicated by the DNA polymerase before termination of polymerization (generally, primer extension) or template switch. For example, with respect to a TSO, it is the position or region in the target sequence that is complementary to the 3' end of the primer extension product prior to switching template from the template polynucleotide to the unhybridized portion of the TSO.

As used herein, the term "change" means to become different in some way, for example to be altered, such as increased or decreased. A detectable change is one that can be detected, such as a change in the intensity, frequency or presence of a signal, such as fluorescence. In particular examples, the detectable change is a reduction in fluorescence intensity.

As used herein, the term "complementary" means binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5' ATCG 3' of one single-stranded (ss) DNA molecule can bond to 3' TAGC 5' of another ssDNA to form a double-stranded (ds) DNA. In this example, the sequence 5' ATCG 3' is the reverse complement of 3' TAGC 5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

As used herein, the term "fluorophore" means a chemical compound, which when excited by exposure to a particular wavelength of light, emits light (fluoresces), for example at a different wavelength of light. Exemplary fluorophores include, but are not limited to: 6-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow, as well as derivatives thereof. Also encompassed by the term "fluorophore" are luminescent molecules, which are chemical compounds which do not require exposure to a particular wavelength of light to fluoresce; luminescent compounds naturally fluoresce. Therefore, the use of luminescent signals can eliminate the need for an external source of electromagnetic radiation, such as a laser.

As used herein, the phrase "hybridization [of a nucleic acid molecule]" means when two complementary nucleic acid molecules undergo an amount of hydrogen bonding to each other. The stringency of hybridization can vary according to the environmental conditions surrounding the nucleic acid molecules, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, N.Y., 1993). Tm is the temperature at which 50% of a given strand of nucleic acid is hybridized to its complementary strand.

As used herein, the term "stringent conditions" encompasses conditions under which hybridization only will occur if there is less than 25% mismatch between the hybridized nucleic acid molecule and the target sequence. Conditions of "moderate stringency" are those under which nucleic acid molecules with more than 25% sequence mismatch will not hybridize; conditions of "medium stringency" are those under which nucleic acid molecules with more than 15% mismatch will not hybridize; conditions of "high stringency" are those under which nucleic acid molecules with more than 10% mismatch will not hybridize; and conditions of "very high stringency" are those under which nucleic molecules with more than 5% mismatch will not hybridize.

Moderately stringent hybridization conditions include those under which hybridization is performed at, for example, about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2×SSC and 0.1% sodium dodecyl sulfate.

Highly stringent hybridization conditions include those under which hybridization is performed at, for example, about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 65° C. with a wash solution containing 0.2×SSC and 0.1% sodium dodecyl sulfate.

The complementary nucleic acid sequences described herein can hybridize under stringent, moderately stringent, and/or highly stringent condition.

As used herein, the term "isolated [biological component]" means a biological component (such as a nucleic acid molecule) which has been substantially separated, produced apart from, or purified away from other biological components. Nucleic acid molecules which have been "isolated" include nucleic acid molecules purified by standard purification methods, as well as those chemically synthesized. Isolated does not require absolute purity, and can include nucleic acid molecules that are at least 50% isolated, such as at least 75%, 80%, 90%, 95%, 98%, 99% or even 100% isolated.

As used herein, the term "label" means an agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part of Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

As used herein, the term "nucleic acid molecule" or "polynucleotide sequence" means a deoxyribonucleotide or ribonucleotide polymer, which can include analogues of natural nucleotides that hybridize to nucleic acid molecules in a manner similar to naturally occurring nucleotides. In a particular example, a nucleic acid molecule or polynucleotide sequence is a single-stranded (ss) DNA or RNA molecule, such as a primer. In another particular example, a nucleic acid molecule or polynucleotide sequence is a double-stranded (ds) DNA, such as a target polynucleotide sequence. The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties and modified phosphate backbones, for example as described in U.S. Pat. No. 5,866,336 to Nazarenko et al. Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl)uracil, and 2,6-diaminopurine.

As used herein, the term "primer" means a short single-stranded polynucleotide, generally with a free 3'-OH group, which, when hybridized to its complementary target nucleic acid, allows strand extension by a polymerase such as reverse transcriptase. Primer pairs bracketing an amplicon can be used for amplification of a nucleic acid sequence, for example by TMA, PCR or other nucleic acid amplification methods. In preferred embodiments, a single composite primer is used, said composite primer comprises (i) a 5' promoter portion, and (ii) a 3' target-recognition portion which is complementary to the 3' end portion of the target polynucleotide sequence, and is no more than 30, 40, 50, 60, 70 or 80, preferably no more than 60, bases in length.

As used herein, the phrase "quantitating [a nucleic acid molecule]" means determining or measuring a quantity (such as a relative quantity) of nucleic acid molecule present, such as the number of nucleic acid molecules present in a sample. In particular examples, it is determining the relative amount or actual number of nucleic acid molecules present in a sample.

As used herein, the term "quenching of fluorescence" means a reduction of fluorescence. For example, quenching of a fluorophore's fluorescence on a sequence occurs when a quencher molecule (such as guanosine) is present in sufficient proximity to the fluorophore that it reduces the fluorescence signal of the reporter molecule during complementary strand synthesis.

As used herein, the term "real-time TMA" means a method for detecting and measuring products generated during the process of TMA, which are proportionate to the amount of target nucleic acid prior to the start of TMA. The information obtained, such as an amplification curve, can be used to quantitate the initial amounts of target nucleic acid.

As used herein, the term "recombinant [nucleic acid molecule]" is a nucleic acid molecule having a sequence that is not naturally occurring or a sequence that is made by an artificial combination of two otherwise separated segments of sequence. This artificial combination can be accomplished, for example, by chemical synthesis or by the artificial manipulation of isolated segments of nucleic acid molecules, for example, by genetic engineering techniques.

As used herein, the term "sample" means biological samples such as samples containing nucleic acid molecules, such as genomic DNA, cDNA, RNA, mRNA, rRNA, or combinations thereof. Samples can be obtained from the cells of a subject, such as those present in peripheral blood, urine, saliva, tissue biopsy, surgical specimen, fine needle aspirates, amniocentesis samples and autopsy material.

As used herein, the term "target-recognition portion" means a nucleotide sequence that can substantially hybridize with a target nucleic acid, such as under a stringent, moderately stringent, or highly stringent condition. In particular examples, such target-recognition portion is at least 5, 10, 15, 20, 30, 40 or more nucleotides long. Preferably, the target-recognition portion is about 15 to 35 nucleotides long.

As used herein, the term "signal" means an indicator, such as a detectable physical quantity from which information can be obtained. In one example, a label emits a signal capable of detection, such as a fluorescent signal.

As used herein, the term "synthesis of [a nucleic acid molecule]" means building up a nucleic acid molecule from its component parts, for example by replicating a nucleic acid molecule or polynucleotide sequence. Examples include, but are not limited to, DNA synthesis and RNA-dependent DNA synthesis using reverse transcriptase.

As used herein, the term "target [nucleic acid molecule]" means a nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule in a cell (which can include host RNAs (such as mRNA) and DNAs (such as genomic or cDNA), as well as other nucleic acid molecules such as viral, bacterial or fungal nucleic acid molecules), the amplification of which is intended. Purification or isolation of the target nucleic acid molecule, if needed, can be conducted by methods known to those in the art, such as by using a commercially available purification kit or the like.

As used herein, the term "upstream" and "downstream" refer to a relative position in DNA or RNA. Each strand of DNA or RNA has a 5' end and a 3' end, so named for the carbons on the deoxyribose ring. Relative to the position on the strand, downstream is the region towards the 3'-end of the strand, and upstream is the region towards the 5' end of the strand. Since DNA strands run in opposite directions, downstream on one strand is upstream on the other strand.

4. BRIEF DESCRIPTION OF THE FIGURES

FIG. 1. Single, short RNA target polynucleotide sequence amplification and detection using a composite primer of the invention, a blocking oligonucleotide, and a detection means.

Figure 2:
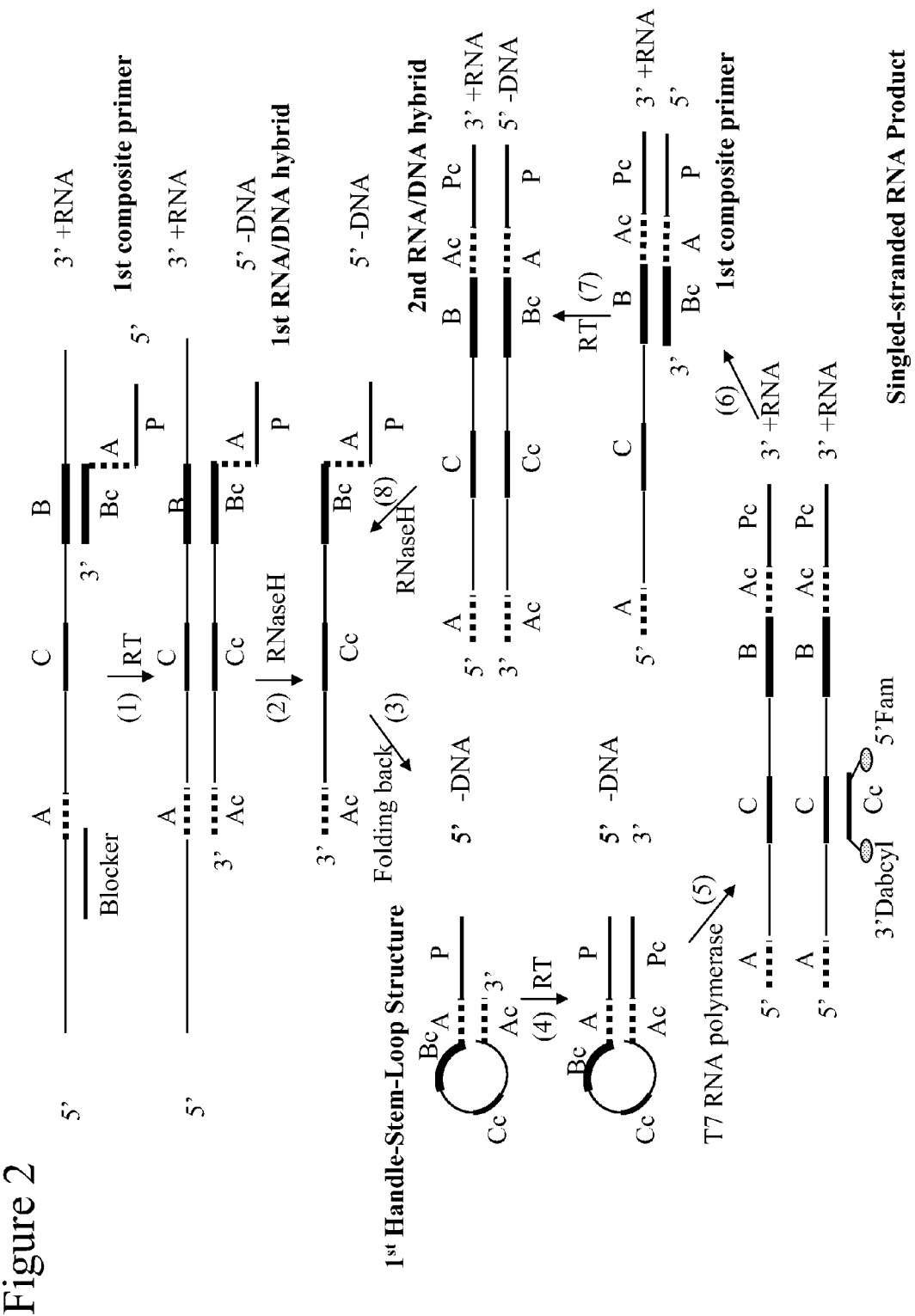

FIG. 2. Single RNA target polynucleotide sequence amplification and detection using a composite primer of the invention, a blocking oligonucleotide, and a detection means.

Figure 3:
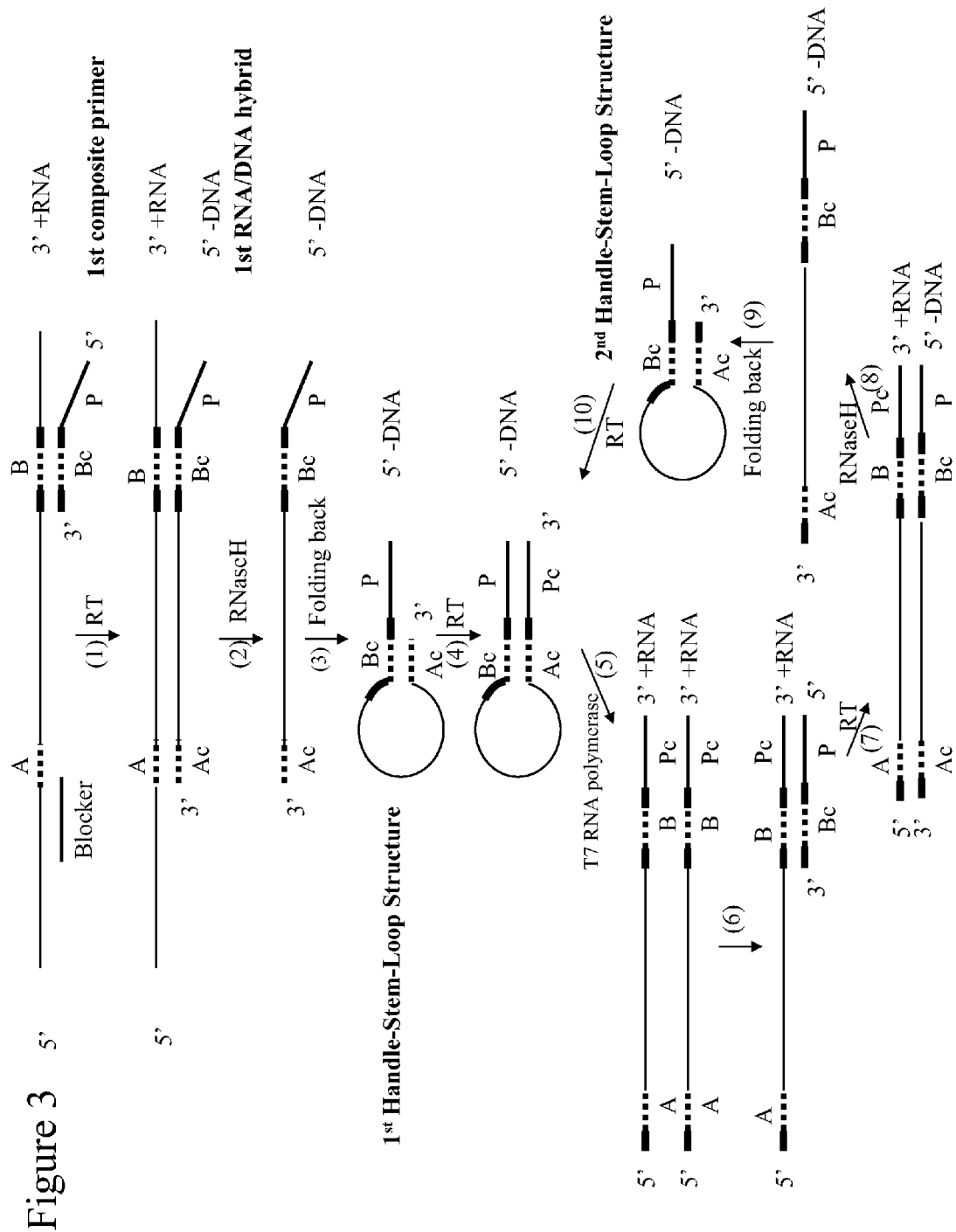

FIG. 3. Single RNA target polynucleotide sequence amplification using a composite primer of the invention and a blocking oligonucleotide.

Figure 4:
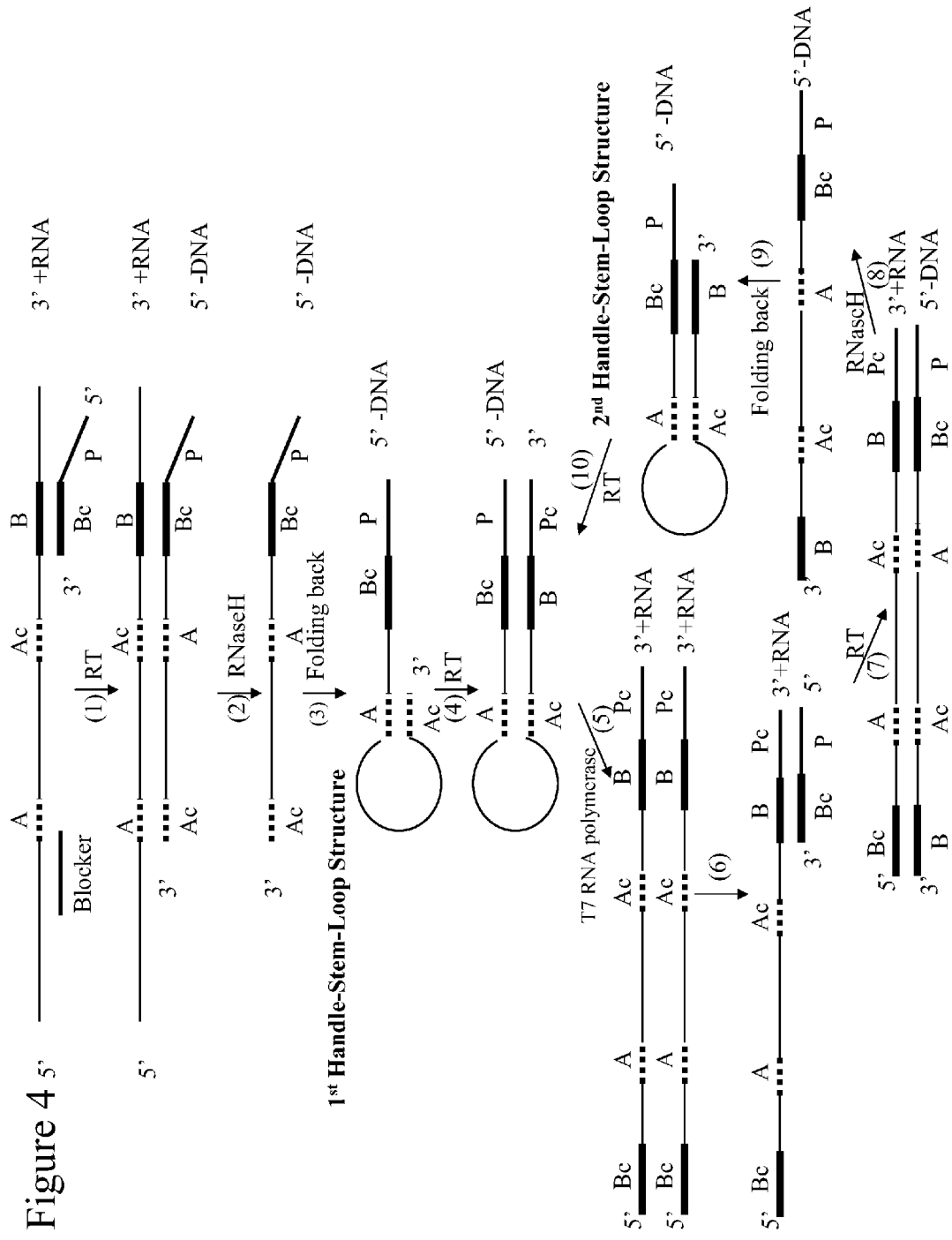

FIG. 4. Single RNA target polynucleotide sequence amplification using a composite primer of the invention and a blocking oligonucleotide.

Figure 5:
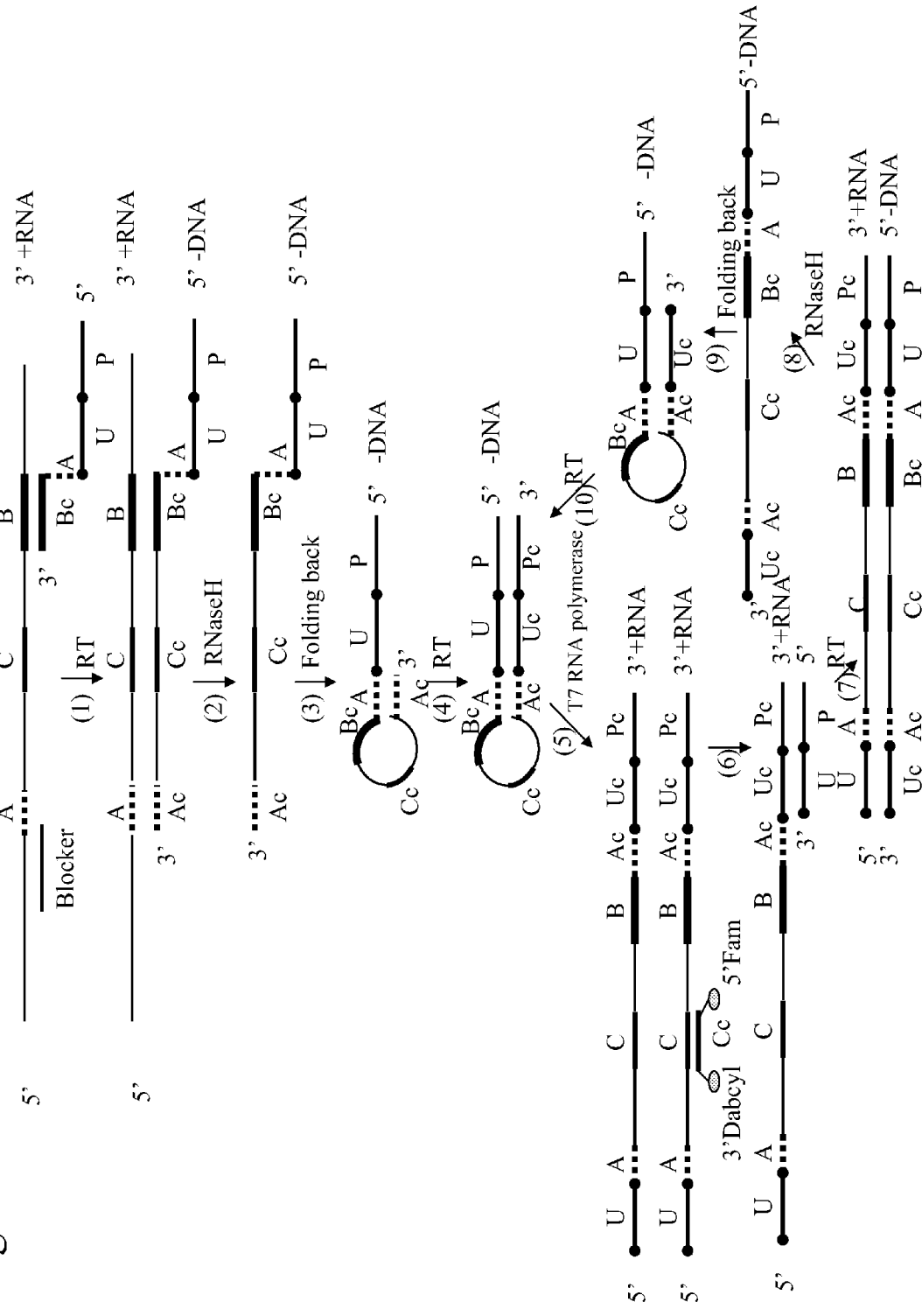

FIG. 5. Single RNA target polynucleotide sequence amplification and detection using a composite primer of the invention, a blocking sequence, a promoter primer comprising a universal sequence, and a detection means.

Figure 6:
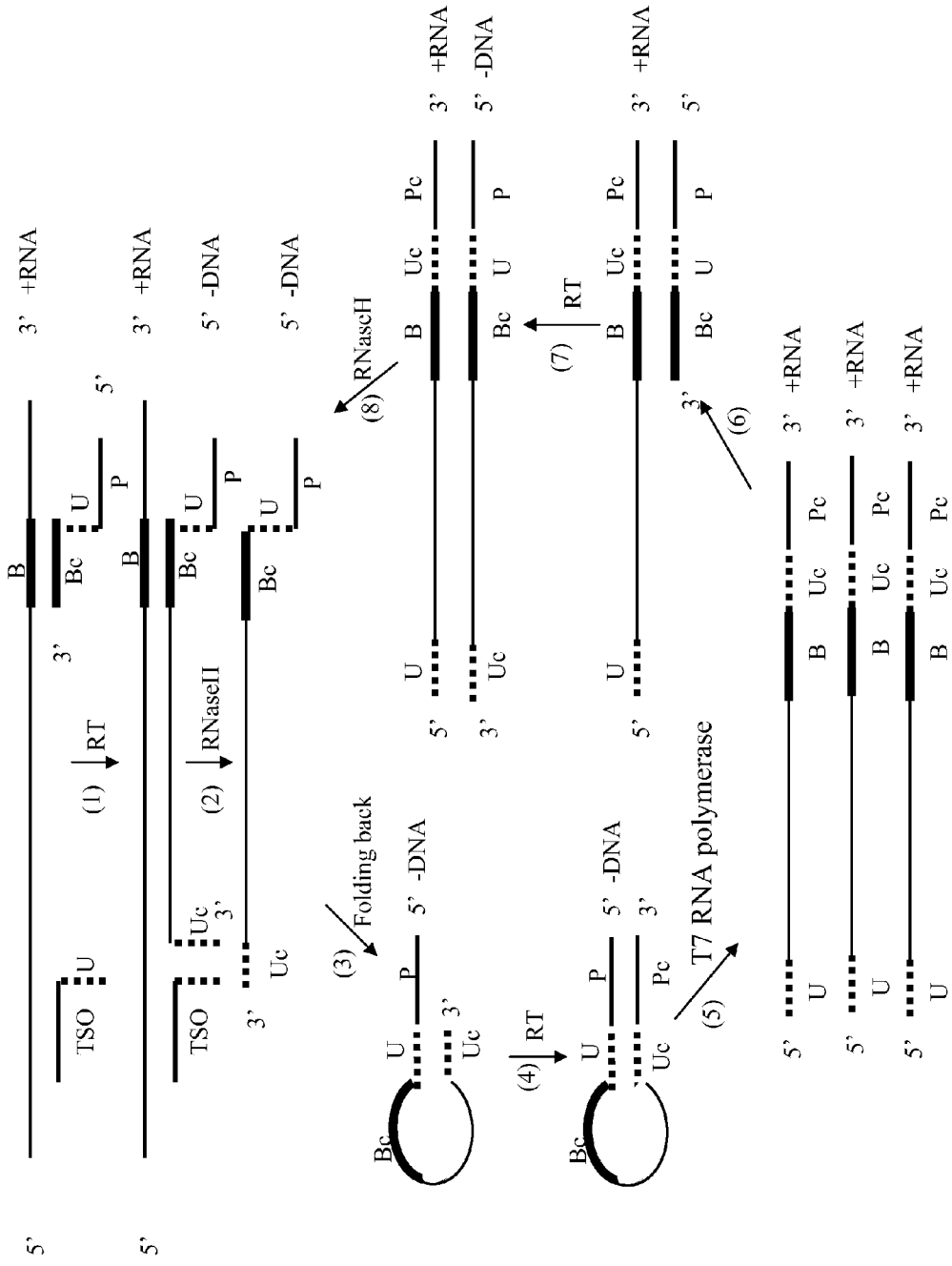

FIG. 6. Single RNA target polynucleotide sequence amplification using a composite primer of the invention and a template switching oligonucleotide (TSO).

Figure 7:
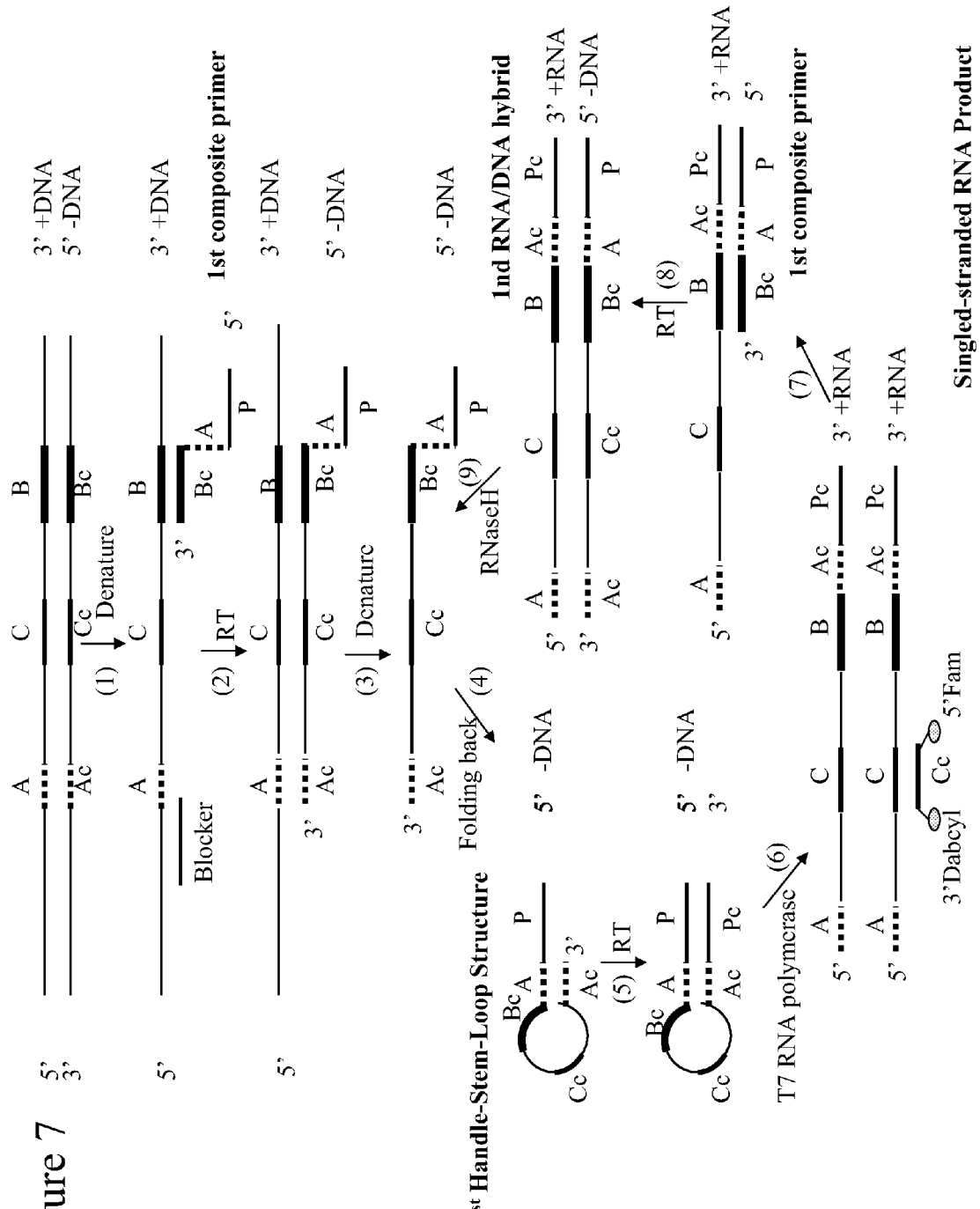

FIG. 7. Single DNA target polynucleotide sequence amplification and detection using a composite primer of the invention, a blocking sequence, and a detection means.

Figure 8:
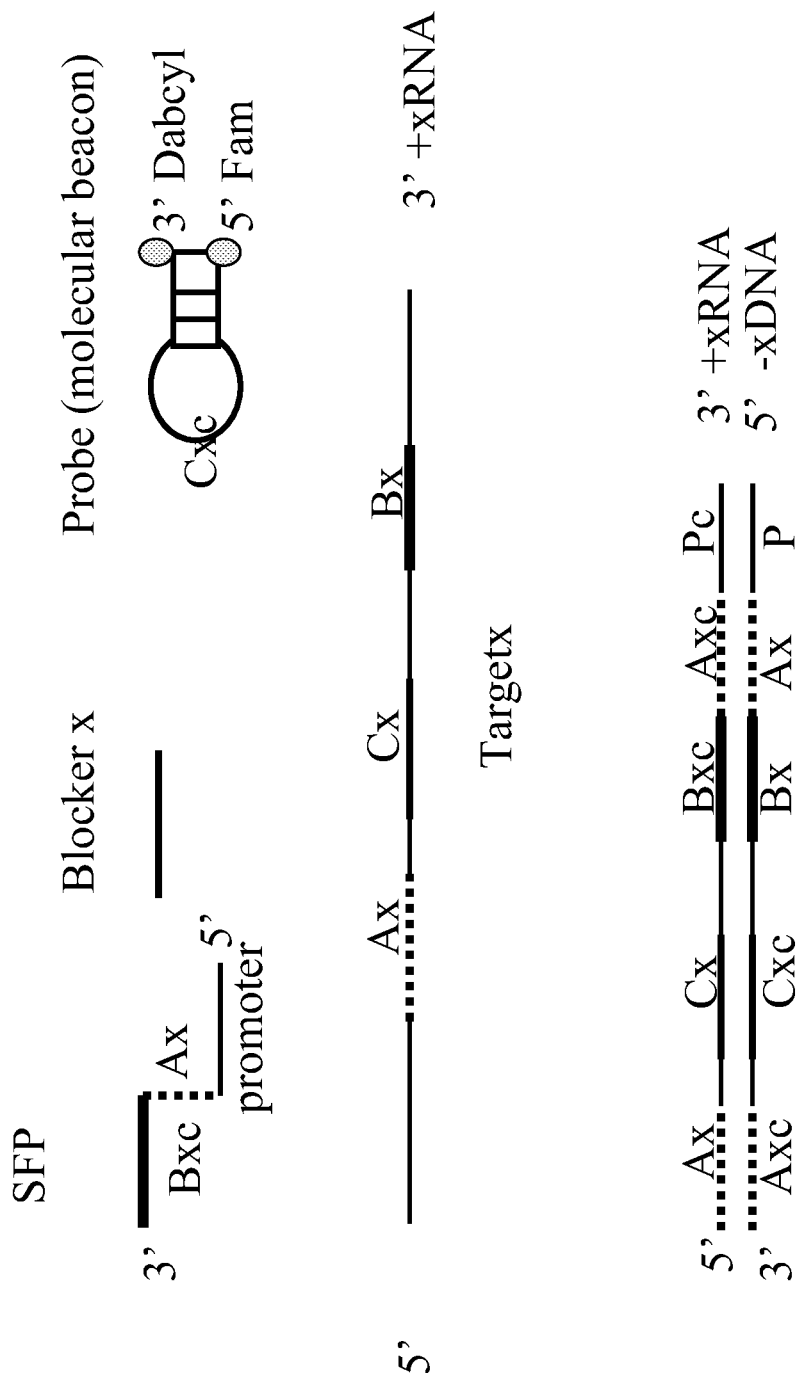

FIG. 8. Generic sequence formula of a composite primer, a blocking sequence, a RNA/DNA hybrid, and a detection means for multiple RNA target polynucleotide sequences amplification and detection using the methods of the invention.

Figure 9:
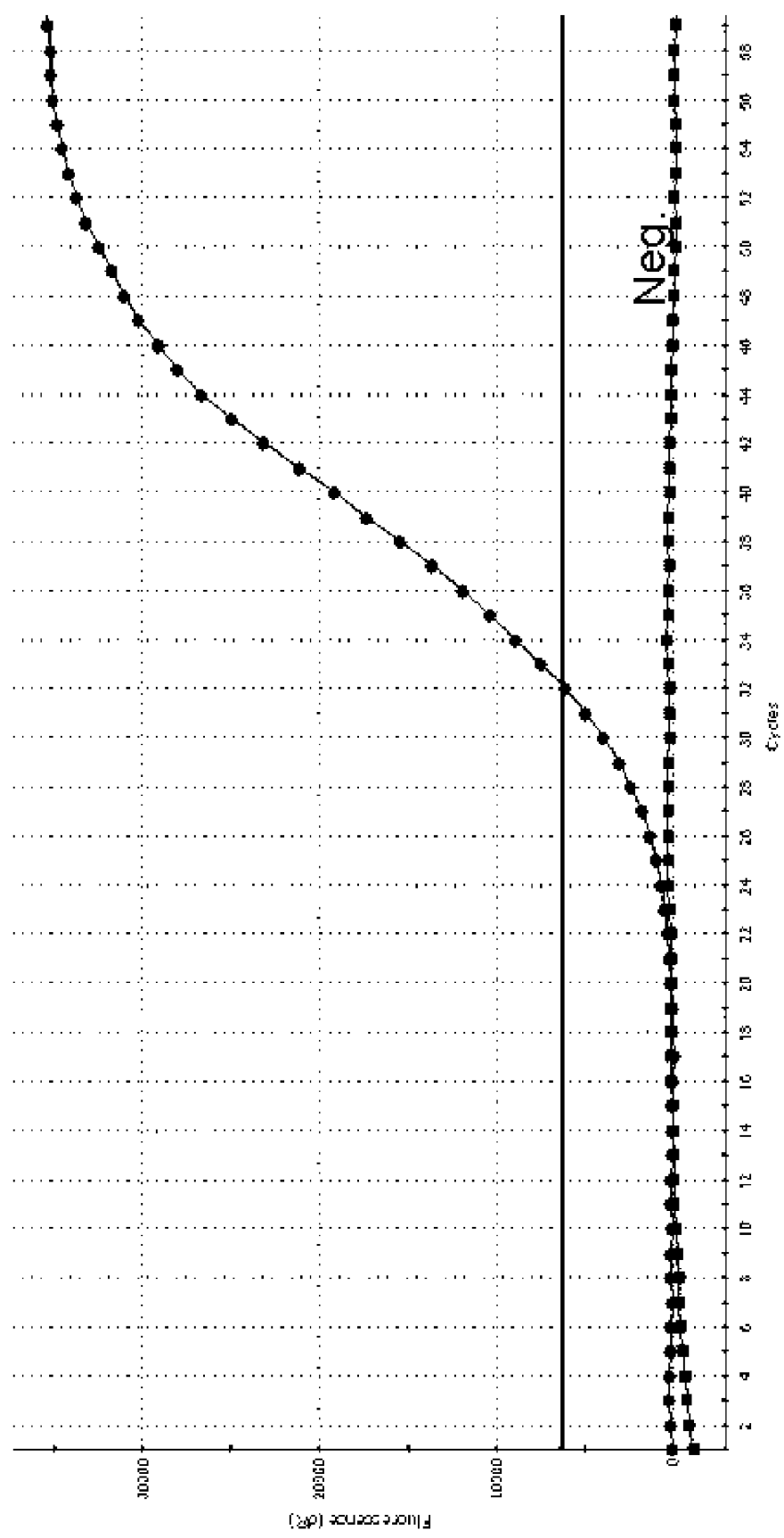

FIG. 9. Raw curve of amplification in which no target (negative control) or 1 pg of HCV RNA were amplified with a composite primer of the invention.

Figure 10:
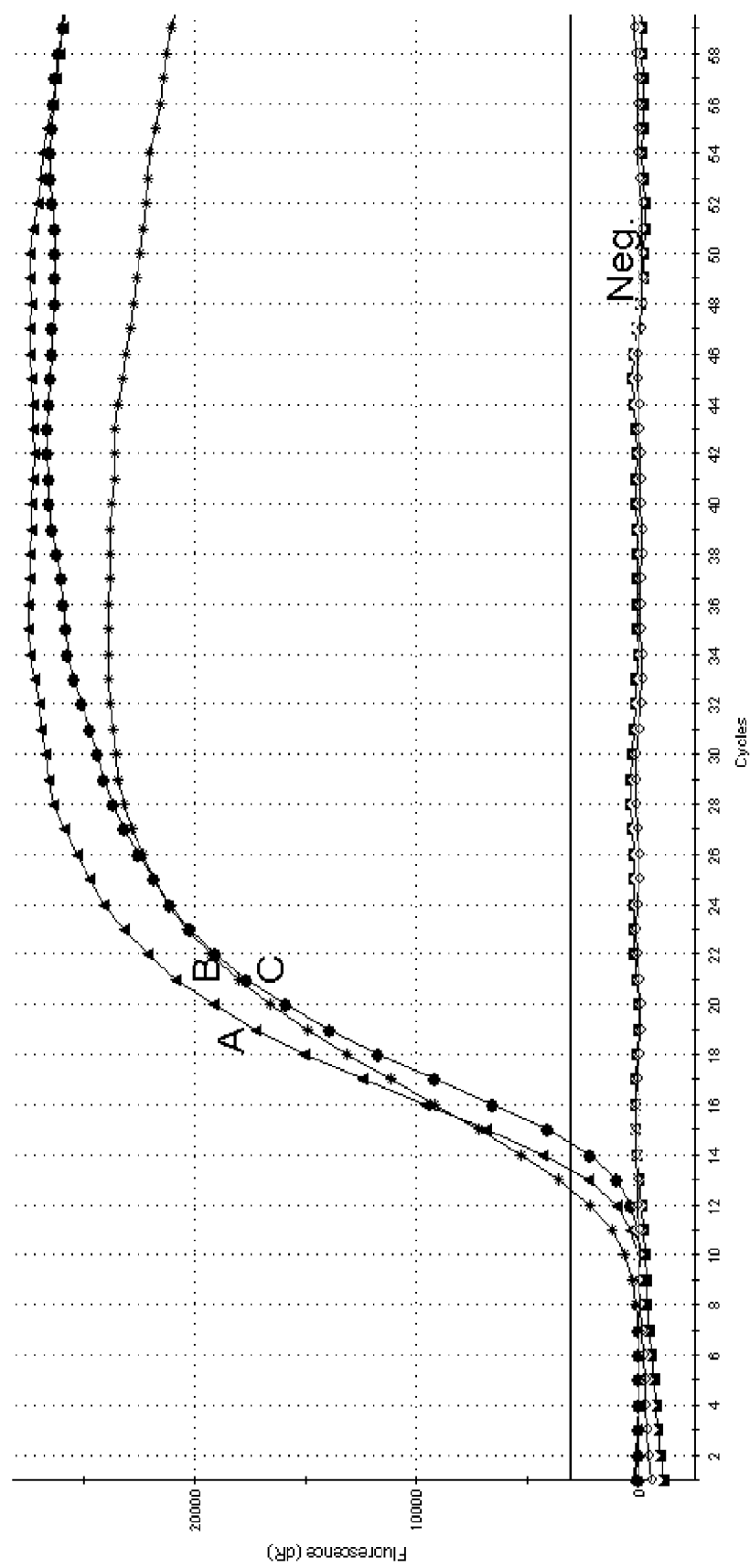

FIG. 10. Raw curve of amplification in which HCV RNA were amplified with composite primers with different length of folding sequence.

Figure 11:
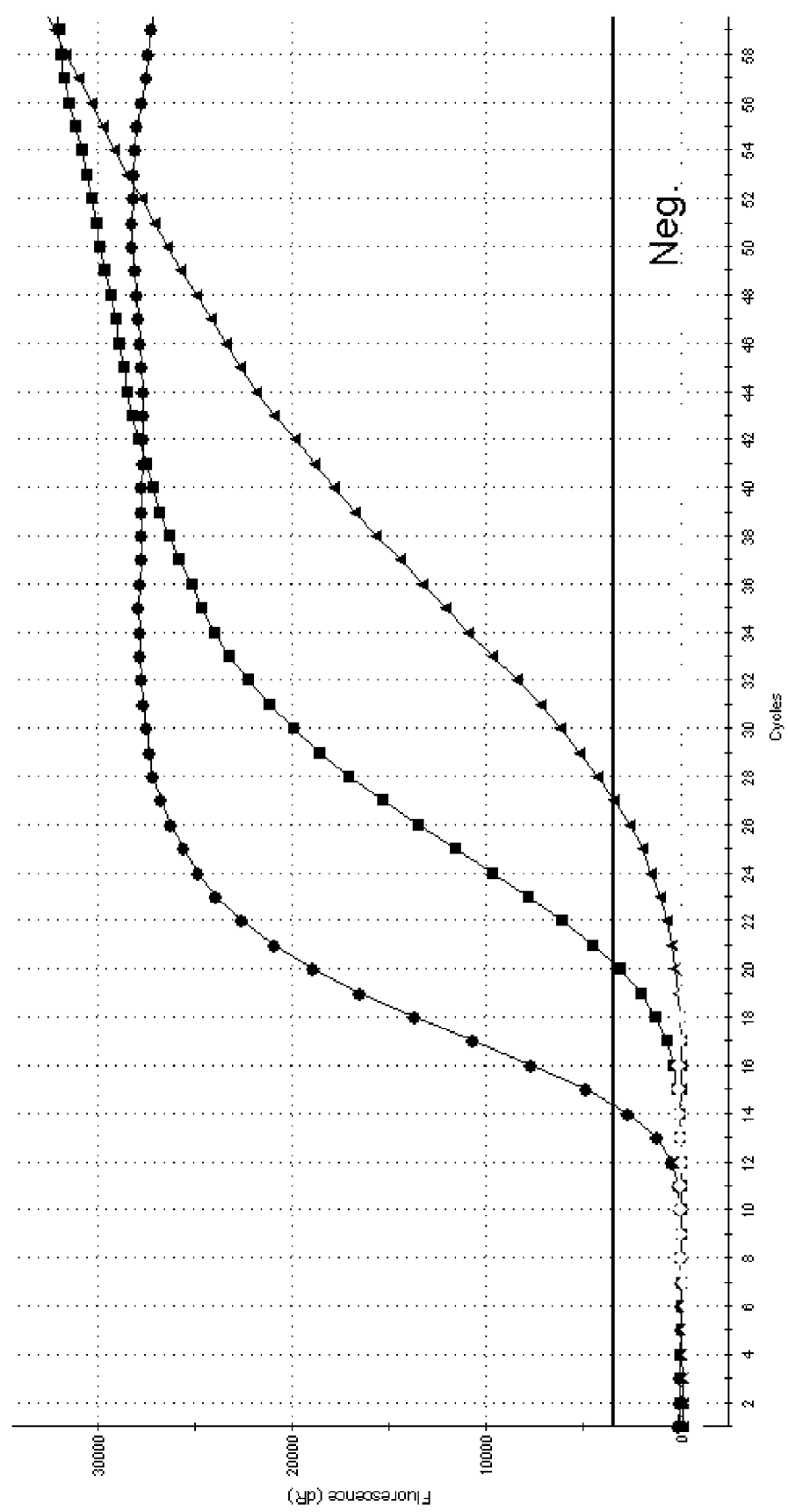

FIG. 11. Raw curve of amplification in which no target (negative control) or 10 pg, 1 pg or 0.1 pg of HCV RNA were amplified with a composite primer of the invention.

5. DETAILED DESCRIPTION OF THE INVENTION

Section 5.1 below describes in detail the composite primer and methods of the invention. Section 5.2 below describes in detail compositions and kit comprising the composite primer and amplified product(s) of the invention.

5.1 Composite Primer and Methods of the Invention

Transcription-mediated amplification (TMA) is an RNA transcription amplification system using two enzymes (i.e., RNA polymerase and reverse transcriptase) and two primers to drive the reaction. One of the primers contains a promoter sequence for RNA polymerase. In a first step, the promoter-primer is hybridized to the target RNA at a defined site. Reverse transcriptase (RT) creates a single-stranded DNA template having a sequence complementary to that of the target RNA by extension from the 3' end of the promoter-primer. The RNA in the resulting RNA/DNA hybrid is degraded by the RNAase H activities of the reverse transcriptase. A second primer then binds to the single-stranded DNA template. A new strand of DNA is synthesized from the end of the second primer by reverse transcriptase, creating a double-stranded DNA molecule. RNA polymerase recognizes the promoter sequence in the double-stranded DNA molecule and initiates transcription. Each of the newly synthesized RNA amplicons re-enters the TMA process and serves as a template for a new round of replication leading to an exponential expansion of the RNA amplicon. Since each of the double-stranded DNA molecule can make 100-1000 copies of RNA amplicons, this expansion can result in the production of 10 billion amplicons in less than an hour. TMA is isothermal; the entire reaction is performed at the same temperature in a water bath or heat block. This is in contrast to other amplification reactions such as polymerase chain reaction (PCR) or ligase chain reaction (LCR) that require a thermal cycler instrument to rapidly change the temperature to drive the reaction.

As discussed above, conventional TMA requires the use of a pair of primers, a first promoter-primer comprising a target-recognition portion which hybridizes to a region of the target nucleic acid, and a second non-promoter primer comprising a region of the target nucleic acid that does not overlap with and is upstream of the region of the target nucleic acid to which the promoter-primer hybridizes.

Thus, TMA typically requires the use of at least two target-specific sequences in primer design and optimization. When amplification and detection involve more than one target nucleic acid, design and optimization of each primer and probe for each target is required. These are costly, time-consuming and often challenging and difficult processes. When the useful sequences of a particular target is limited, it is difficult to design two sequence-specific primers.

In contrast, the present invention requires use of a single primer, which is advantageous for a number of reasons. First, the need of one sequence-specific primer facilitates the design of the primer especially in those cases where the useful sequence of a particular target is limited. Also, when only one primer is used the amplification process, unintended amplification products are less likely to form. In addition, since only one primer is needed per target, optimization of a reaction system is much easier, especially in multiplex amplification and detection. Sometimes, secondary structures are present in certain areas of the target sequence, making such areas not desirable for use in primer design. For example, in TMA systems, a helper oligonucleotide would be required to open up these secondary structure in order to increase amplification efficiency. However, these areas can be included in the composite primer of the present invention, since the secondary structure can be useful to facilitate the formation of the self-folding handle-stem-loop product.

The present invention uses a single primer, i.e., a composite primer, in the amplification process. The composite primer comprises (i) a 5' promoter portion (P) and (ii) a 3' target-recognition portion which is complementary to the 3' end portion of a target polynucleotide sequence (T), which is sometimes within a longer polynucleotide template. In a first step, the composite primer hybridizes to the target polynucleotide sequence. At the same time or shortly thereafter, the 5' end of the target polynucleotide sequence is identified. If the target polynucleotide sequence is a short target sequence as described above, then the '5 end of the target polynucleotide sequence is simply the natural 5' end. If the target polynucleotide sequence is within a longer polynucleotide template, then the 5' end of the target polynucleotide sequence is identified either by using an enzyme to cut, nick or cleave at a region of the polynucleotide template, or by hybridizing a nucleotide sequence (e.g., a blocking oligonucleotide or template switching oligonucleotide (TSO)) to a region of the polynucleotide template, which is immediately upstream of the 5' end of the target polynucleotide sequence. Reverse transcriptase (RT) then creates a single-stranded DNA template having a sequence complementary to that of the target polynucleotide sequence by extension from the 3' end of the composite primer. The RNA in the resulting RNA/DNA hybrid is degraded by the RNAase H activities of the reverse transcriptase. The remaining single-stranded DNA template comprises the promoter portion (P) and the complementary sequence of the target polynucleotide sequence (Tc). In particular, the single-stranded DNA comprises a pair of self-folding segments that are complementary to and sometimes separated from each other, wherein the promoter portion (P) is at the 5' end of the single-stranded DNA template and one of the self-folding segments is at the 3' end of the single-stranded DNA template. The single-stranded DNA template self-folds and forms a handle-stem-loop structure which comprises a 5' single-stranded handle comprising the promoter portion (P), a double-stranded stem comprising the pair of self-folding segments hybridized to each other, and a single-stranded loop comprising the sequence between the pair of self-folding segments. Reverse transcriptase then extends the 3' end of the handle-stem-loop structure, creating a double-stranded handle with a promoter sequence. RNA polymerase recognizes the promoter sequence and initiates transcription, generating multiple copies of a single-stranded RNA product comprising the target polynucleotide sequence (T) and sometimes also comprising the complementary sequence of the promoter portion (Pc) at the 3' end.

Each of the newly synthesized single-stranded RNA product (also known as "RNA amplicons") re-enters the TMA process and serves as a template for a new round of replication. In particular, the same composite primer (or sometimes a shorter version thereof, preferably including a universal sequence not found in the target polynucleotide sequence or its complementary sequence) hybridizes to the single-stranded RNA product. Reverse transcriptase then creates the single-stranded DNA template of the single-stranded RNA product by extension from the 3' end of the composite primer. The RNA in the resulting RNA/DNA hybrid is degraded by the RNAase H activities of the reverse transcriptase. The remaining single-stranded DNA template comprises the promoter portion (P) and the complementary sequence of the target polynucleotide sequence (Tc), and similarly comprises the pair of self-folding segments that are complementary to and separated from each other. Once the single-stranded DNA template self-folds and forms the handle-stem-loop structure, reverse transcriptase extends the 3' end of the handle-stem-loop structure, creating a double-stranded handle with a promoter sequence which is recognized by RNA polymerase to initiate transcription, generating multiple copies of the single-stranded RNA.

As illustrated in FIGS. 1-7, a single composite primer is sufficient for amplification of a target polynucleotide sequence (RNA in FIGS. 1-6 and DNA in FIG. 7) in a TMA system.

In certain embodiments, the method is for amplification of a short target polynucleotide sequence not within a longer polynucleotide template (see FIG. 1).

The method illustrated in FIG. 1 uses a composite primer which comprises (i) a 5' promoter portion (P), (ii) a 3' target-recognition portion (Bc) which is complementary to the 3' end portion (B) of a target polynucleotide sequence (T), and (iii) between the promoter portion (P) and the 3' target-recognition portion (Bc), a segment corresponding to a 5' end portion (A) of the target polynucleotide sequence, wherein this segment and its complementary sequence (Ac) form a pair of self-folding segments. In a first step (1), the target polynucleotide sequence (+) is hybridized with the composite primer (−), and the 5' end (A) of the target polynucleotide sequence is the natural 5' end of the target polynucleotide sequence. Then, the 3' end of the composite primer is extended to generate a first RNA/DNA hybrid. In a second step (2), the RNA portion is removed to generate a single-stranded DNA template (−) comprising the promoter portion (P) and the complementary sequence of the target polynucleotide sequence (Tc), said single-stranded DNA template also comprising the pair of self-folding segments (i.e., A and Ac), wherein the promoter portion (P) is at the 5' end of the single-stranded DNA template and one of the self-folding segments (i.e., Ac) is at the 3' end of the single-stranded DNA template. In a third step (3), the single-stranded DNA template is allowed to self-fold and form a handle-stem-loop structure, which comprises a 5' single-stranded handle comprising the promoter portion (P), a double-stranded stem comprising the pair of self-folding segments (i.e., A and Ac) hybridized to each other, and a single-stranded loop comprising the sequence between the pair of self-folding segments. In a fourth step (4), the 3' end of the handle-stem-loop structure is extended to generate a double-stranded promoter comprising the promoter portion (P) and its complementary sequence (Pc) hybridized to each other. In a fifth step (5), transcription is initiated from the double-stranded promoter to generate multiple copies of a single-stranded RNA product (+) comprising the target polynucleotide sequence (T) and the complementary sequence of the promoter portion (Pc), wherein the complementary sequence of the promoter portion (Pc) is at the 3' end of the single-stranded RNA product. In a sixth step (6), the single-stranded RNA product is hybridized with the composite primer. In a seventh step (7), the 3' end of the composite primer is extended to generate a second RNA/DNA hybrid. In an eighth step (8), the RNA portion is removed from the second RNA/DNA hybrid to generate the single-stranded DNA template. Steps (3), (4) and (5) are continued in order to exponentially generate multiple copies of the single-stranded RNA product. The single-stranded RNA product can be detected using, for example, a molecular beacon comprising a sequence complementary to a portion of the target polynucleotide sequence, wherein said sequence is not found in the composite primer or the 5' end portion of the target polynucleotide sequence, or their respective complementary sequences.

In certain embodiments, the method comprises identifying the 5' end of the target polynucleotide sequence with the use of a blocking oligonucleotide ("blocker"). FIGS. 2-4 illustrates the amplification and detection of a single RNA target polynucleotide sequence using a composite primer of the invention and a blocking oligonucleotide. The method illustrated in FIG. 2 uses a composite primer which comprises (i) a 5' promoter portion (P), (ii) a 3' target-recognition portion (Bc) which is complementary to the 3' end portion (B) of a target polynucleotide sequence (T), which is within a longer polynucleotide template, and (iii) between the promoter portion (P) and the 3' target-recognition portion (Bc), a segment corresponding to a 5' end portion (A) of the target polynucleotide sequence, wherein this segment and its complementary sequence (Ac) form a pair of self-folding segments. In a first step (1), the target polynucleotide sequence (+) is hybridized with the composite primer (−), and the 5' end (A) of the target polynucleotide sequence is identified by hybridizing a blocking oligonucleotide ("blocker") to a region of the polynucleotide template immediately upstream of the 5' end (A) of the target polynucleotide sequence. Then, the 3' end of the composite primer is extended to generate a first RNA/DNA hybrid. In a second step (2), the RNA portion is removed to generate a single-stranded DNA template (−) comprising the promoter portion (P) and the complementary sequence of the target polynucleotide sequence (Tc), said single-stranded DNA template also comprising the pair of self-folding segments (i.e., A and Ac), wherein the promoter portion (P) is at the 5' end of the single-stranded DNA template and one of the self-folding segments (i.e., Ac) is at the 3' end of the single-stranded DNA template. In a third step (3), the single-stranded DNA template is allowed to self-fold and form a handle-stem-loop structure, which comprises a 5' single-stranded handle comprising the promoter portion (P), a double-stranded stem comprising the pair of self-folding segments (i.e., A and Ac) hybridized to each other, and a single-stranded loop comprising the sequence between the pair of self-folding segments. In a fourth step (4), the 3' end of the handle-stem-loop structure is extended to generate a double-stranded promoter comprising the promoter portion (P) and its complementary sequence (Pc) hybridized to each other. In a fifth step (5), transcription is initiated from the double-stranded promoter to generate multiple copies of a single-stranded RNA product (+) comprising the target polynucleotide sequence (T) and the complementary sequence of the promoter portion (Pc), wherein the complementary sequence of the promoter portion (Pc) is at the 3' end of the single-stranded RNA product. In a sixth step (6), the single-stranded RNA product is hybridized with the composite primer. In a seventh step (7), the 3' end of the composite primer is extended to generate a second RNA/DNA hybrid. In an eighth step (8), the RNA portion is removed from the second RNA/DNA hybrid to generate the single-stranded DNA template. Steps (3), (4) and (5) are continued in order to exponentially generate multiple copies of the single-stranded RNA product. The single-stranded RNA product can be detected using, for example, a molecular beacon comprising a sequence complementary to a portion of the target polynucleotide sequence, wherein said sequence is not found in the composite primer or the 5' end portion of the target polynucleotide sequence, or their respective complementary sequences.

The method illustrated in FIG. 3 uses a composite primer which comprises (i) a 5' promoter portion (P), and (ii) a 3' target-recognition portion (Bc) which is complementary to the 3' end portion (B) of a target polynucleotide sequence (T), which is within a longer polynucleotide template, wherein the 3' target-recognition portion (Bc) comprises a segment corresponding to a 5' end portion (A) of the target polynucleotide sequence, and together, said segment and its complementary sequence form a first pair of self-folding segments. In a first step (1), the target polynucleotide sequence (+) is hybridized with the composite primer (−), and the 5' end (A) of the target polynucleotide sequence is identified by hybridizing a blocking oligonucleotide ("blocker") to a region of the polynucleotide template immediately upstream of the 5' end of the target polynucleotide sequence. Then, the 3' end of the composite primer is extended to generate a first RNA/DNA hybrid. In a second step (2), the RNA portion is removed to generate a first single-stranded DNA template (−) comprising the promoter portion (P) and the complementary sequence of the target polynucleotide sequence (Tc), said first single-stranded DNA template also comprising the first pair of self-folding segments, wherein the promoter portion (P) is at the 5' end of the first single-stranded DNA template and one of the self-folding segments is at the 3' end of the first single-stranded DNA template. In a third step (3), the first single-stranded DNA template is allowed to self-fold and form a first handle-stem-loop structure, which comprises a 5' single-stranded handle comprising the promoter portion (P), a double-stranded stem comprising the first pair of self-folding segments hybridized to each other, and a single-stranded loop comprising the sequence between the first pair of self-folding segments. In a fourth step (4), the 3' end of the first handle-stem-loop structure is extended to generate a double-stranded promoter comprising the promoter portion (P) and its complementary sequence (Pc) hybridized to each other. In a fifth step (5), transcription is initiated from the double-stranded promoter to generate multiple copies of a single-stranded RNA product (+) comprising the target polynucleotide sequence (T) and the complementary sequence of the promoter portion (Pc), wherein the complementary sequence of the promoter portion (Pc) is at the 3' end of the single-stranded RNA product. In a sixth step (6), the single-stranded RNA product is hybridized with the composite primer. In a seventh step (7), the 3' end of the composite primer is extended to generate a second RNA/DNA hybrid. In an eighth step (8), the RNA portion is removed from the second RNA/DNA hybrid to generate a second single-stranded DNA template (−) comprising the promoter portion (P) and the complementary sequence of the target polynucleotide sequence (Tc), said second single-stranded DNA template also comprising a second pair of self-folding segments that are complementary to and separated from each other, wherein the promoter portion (P) is at the 5' end of the second single-stranded DNA template and one of the second pair of self-folding segments is at the 3' end of the second single-stranded DNA template. In a ninth step (9), the second single-stranded DNA template is allowed to self-fold and form a second handle-stem-loop structure, which comprises a 5' single-stranded handle comprising the promoter portion (P), a double-stranded stem comprising the second pair of self-folding segments hybridized to each other, and a single-stranded loop comprising the sequence between the second pair of self-folding segments. In a tenth step (10), the 3' end of the second handle-stem-loop structure is extended to generate a double-stranded promoter comprising the promoter portion (P) and its complementary sequence (Pc) hybridized to each other. Transcription is initiated from the double-stranded promoter to generate multiple copies of the single-stranded RNA product.

The method illustrated in FIG. 4 uses a composite primer which comprises (i) a 5' promoter portion (P), and (ii) a 3' target-recognition portion (Bc) which is complementary to the 3' end portion (B) of a target polynucleotide sequence (T), which is within a longer polynucleotide template. The target polynucleotide sequence comprises a first pair of self-folding segments which comprise a segment corresponding to a 5' end portion (A) of the target polynucleotide sequence and its complementary sequence (Ac) located at a separate portion of the target polynucleotide sequence. In a first step (1), the target polynucleotide sequence (+) is hybridized with the composite primer (−), and the 5' end of the target polynucleotide sequence is identified by hybridizing a blocking oligonucleotide ("blocker") to a region of the polynucleotide template immediately upstream of the 5' end of the target polynucleotide sequence. Then, the 3' end of the composite primer is extended to generate a first RNA/DNA hybrid. In a second step (2), the RNA portion is removed to generate a first single-stranded DNA template (−) comprising the promoter portion (P) and the complementary sequence of the target polynucleotide sequence (Tc), said first single-stranded DNA template also comprising the first pair of self-folding segments (i.e., A and Ac), wherein the promoter portion (P) is at the 5' end of the first single-stranded DNA template and one of the self-folding segments is at the 3' end of the first single-stranded DNA template. In a third step (3), the first single-stranded DNA template is allowed to self-fold and form a first handle-stem-loop structure, which comprises a 5' single-stranded handle comprising the promoter portion (P) and the 3' target-recognition portion (Bc), a double-stranded stem comprising the first pair of self-folding segments (i.e., A and Ac) hybridized to each other, and a single-stranded loop comprising the sequence between the first pair of self-folding segments. In a fourth step (4), the 3' end of the first handle-stem-loop structure is extended to generate a double-stranded promoter comprising the promoter portion (P) and its complementary sequence (Pc) hybridized to each other. In a fifth step (5), transcription is initiated from the double-stranded promoter to generate multiple copies of a single-stranded RNA product (+) comprising, from 5' to 3', the 3' end target-recognition portion (Bc) of the composite primer, the target polynucleotide sequence (T), and the complementary sequence of the promoter portion (Pc), wherein the complementary sequence of the promoter portion (Pc) is at the 3' end of the single-stranded RNA product. In a sixth step (6), the single-stranded RNA product is hybridized with the composite primer. In a seventh step (7), the 3' end of the composite primer is extended to generate a second RNA/DNA hybrid. In an eighth step (8), the RNA portion is removed from the second RNA/DNA hybrid to generate a second single-stranded DNA template(−) comprising the promoter portion (P) and the complementary sequence of the target polynucleotide sequence (Tc), said second single-stranded DNA template also comprising a second pair of self-folding segments (i.e., B and Bc) that are complementary to and separated from each other, wherein the promoter portion (P) is at the 5' end of the second single-stranded DNA template and one of the second pair of self-folding segments is at the 3' end of the second single-stranded DNA template. In a ninth step (9), the second single-stranded DNA template is allowed to self-fold and form a second handle-stem-loop structure, which comprises a 5' single-stranded handle comprising the promoter portion (P), a double-stranded stem comprising the second pair of self-folding segments hybridized to each other, and a single-stranded loop comprising the sequence between the second pair of self-folding segments. In a tenth step (10), the 3' end of the second handle-stem-loop structure is extended to generate a double-stranded promoter comprising the promoter portion (P) and its complementary sequence (Pc) hybridized to each other. Transcription is initiated from the double-stranded promoter to generate multiple copies of the single-stranded RNA product.

The method illustrated in FIG. 5 uses a composite primer which comprises (i) a 5' promoter portion (P), (ii) a 3' target-recognition portion (Bc) which is complementary to the 3' end portion (B) of a target polynucleotide sequence (T), which is within a longer polynucleotide template, and from 5' to 3' and between the promoter portion (P) and the 3' target-recognition portion (Bc), (iii) a universal portion (U) that is not present in the target polynucleotide sequence or its complementary sequence, and (iv) a segment corresponding to a 5' end portion (A) of the target polynucleotide sequence, wherein this segment and its complementary sequence (Ac) form a first pair of self-folding segments. In a first step (1), the target polynucleotide sequence (+) is hybridized with the composite primer (−), and the 5' end (A) of the target polynucleotide sequence is identified by hybridizing a blocking sequence ("blocker") to a region of the polynucleotide template immediately upstream of the 5' end (A) of the target polynucleotide sequence. Then, the 3' end of the composite primer is extended to generate a first RNA/DNA hybrid. In a second step (2), the RNA portion is removed to generate a first single-stranded DNA template (−) comprising the promoter portion (P), the universal portion (U), and the complementary sequence of the target polynucleotide sequence (Tc), said first single-stranded DNA template also comprising the first pair of self-folding segments (i.e., A and Ac), wherein the promoter portion (P) is at the 5' end of the single-stranded DNA template and one of the self-folding segments (i.e., Ac) is at the 3' end of the single-stranded DNA template. In a third step (3), the first single-stranded DNA template is allowed to self-fold and form a first handle-stem-loop structure, which comprises a 5' single-stranded handle comprising the promoter portion (P) and the universal portion (U), a double-stranded stem comprising the pair of self-folding segments (i.e., A and Ac) hybridized to each other, and a single-stranded loop comprising the sequence between the pair of self-folding segments. In a fourth step (4), the 3' end of the handle-stem-loop structure is extended to generate a double-stranded promoter comprising the promoter portion (P) and its complementary sequence (Pc) hybridized to each other. In a fifth step (5), transcription is initiated from the double-stranded promoter to generate multiple copies of a single-stranded RNA product (+) comprising the target polynucleotide sequence (T) and the complementary sequence of the promoter portion (Pc), wherein the complementary sequence of the promoter portion (Pc) is at the 3' end of the single-stranded RNA product. In a sixth step (6), the single-stranded RNA product is hybridized with the composite primer. Alternatively, the single-stranded RNA product is hybridized with a shorter composite primer consisting of, preferably consisting essentially of, the promoter portion (P) and the universal portion (U). In a seventh step (7), the 3' end of the composite primer is extended to generate a second RNA/DNA hybrid. In an eighth step (8), the RNA portion is removed from the second RNA/DNA hybrid to generate a second single-stranded DNA template. In a ninth step (9), the second single-stranded DNA template is allowed to self-fold and form a second handle-stem-loop structure, which comprises a 5' single-stranded handle comprising the promoter portion (P), a double-stranded stem comprising the second pair of self-folding segments (i.e., U and Uc) hybridized to each other, and a single-stranded loop comprising the sequence between the second pair of self-folding segments. In a tenth step (10), the 3' end of the second handle-stem-loop structure is extended to generate a double-stranded promoter comprising the promoter portion (P) and its complementary sequence (Pc) hybridized to each other. Transcription is initiated from the double-stranded promoter to generate multiple copies of the single-stranded RNA product. The single-stranded RNA product can be detected using, for example, a molecular beacon comprising a sequence complementary to a portion of the target polynucleotide sequence, wherein said sequence is not found in the composite primer, the 5' end portion of the target polynucleotide sequence, the universal portion, or their respective complementary sequences.

In certain embodiments, the method comprises introducing defined sequences at the 5' end of the target polynucleotide sequence with the use of a template switching oligonucleotide (TSO) (see, e.g., FIG. 6). Methods for introducing defined sequences at one end of a sequence are well known to one skilled in the art (see, e.g., U.S. Pat. No. 5,679,512 to Laney et al.; and U.S. Pat. No. 6,251,639 to Kurn).

The method illustrated in FIG. 6 uses a composite primer which comprises (i) a 5' promoter portion (P), (ii) a 3' target-recognition portion (Bc) which is complementary to the 3' end portion (B) of a target polynucleotide sequence (T), which is within a longer polynucleotide template, and (iii) between the promoter portion (P) and the 3' target-recognition portion (Bc), a universal portion (U) that is not present in the target polynucleotide sequence or its complementary sequence, wherein the universal portion (U) and its complementary sequence (Uc) form a pair of self-folding segments. In a first step (1), the target polynucleotide sequence (+) is hybridized with the composite primer (−), and the 5' end (A) of the target polynucleotide sequence is identified by hybridizing a template switching oligonucleotide (TSO), which comprises the universal portion (U), to a region of the polynucleotide template immediately upstream of the 5' end (A) of the target polynucleotide sequence. Then, the 3' end of the composite primer is extended to generate a first RNA/DNA hybrid. In a second step (2), the RNA portion is removed to generate a single-stranded DNA template (−) comprising, from 5' to 3', the promoter portion (P), the complementary sequence of the target polynucleotide sequence (Tc), and the complementary sequence of the universal portion (U), said single-stranded DNA template also comprising the pair of self-folding segments (i.e., U and Uc), wherein the promoter portion (P) is at the 5' end of the single-stranded DNA template and one of the self-folding segments (i.e., Uc) is at the 3' end of the single-stranded DNA template. In a third step (3), the single-stranded DNA template is allowed to self-fold and form a handle-stem-loop structure, which comprises a 5' single-stranded handle comprising the promoter portion (P), a double-stranded stem comprising the pair of self-folding segments (i.e., U and Uc) hybridized to each other, and a single-stranded loop comprising the sequence between the pair of self-folding segments. In a fourth step (4), the 3' end of the handle-stem-loop structure is extended to generate a double-stranded promoter comprising the promoter portion (P) and its complementary sequence (Pc) hybridized to each other. In a fifth step (5), transcription is initiated from the double-stranded promoter to generate multiple copies of a single-stranded RNA product (+) comprising the target polynucleotide sequence (T) and the complementary sequence of the promoter portion (Pc), wherein the complementary sequence of the promoter portion (Pc) is at the 3' end of the single-stranded RNA product. In a sixth step (6), the single-stranded RNA product is hybridized with the composite primer. In a seventh step (7), the 3' end of the composite primer is extended to generate a second RNA/DNA hybrid. In an eighth step (8), the RNA portion is removed from the second RNA/DNA hybrid to generate the single-stranded DNA template. Steps (3), (4), (5) and (6) are continued in order to exponentially generate multiple copies of the single-stranded RNA product.

As illustrated in FIG. 7, the methods of the invention are also useful for amplification of one or more DNA target polynucleotide sequence. In a first step (1), a double-stranded DNA duplex is denatured to generate a single-stranded DNA polynucleotide template comprising the target polynucleotide sequence (+). In a second step (2), a composite primer (−) comprising, from 5' to 3', (i) a 5' promoter portion (P), (ii) a segment corresponding to a 5' end portion (A) of the target polynucleotide sequence, and (iii) a 3' target-recognition portion which is complementary to the 3' end portion of a target polynucleotide sequence (T), is hybridized to the target polynucleotide sequence, and the 5' end (A) of the target polynucleotide sequence is identified by hybridizing a blocking oligonucleotide to a region of the polynucleotide template immediately upstream of the 5' end of the target polynucleotide sequence. Then, the 3' end of the target polynucleotide sequence is extended to generate a DNA/DNA hybrid. In a third step (3), the DNA/DNA hybrid is denatured to generate a single-stranded DNA template (−) comprising, from 5' to 3', the promoter portion (P), the segment corresponding to the 5' end portion (A) of the target polynucleotide sequence, and the complementary sequence of the target polynucleotide sequence (Tc). In a fourth step (4), the single-stranded DNA template is allowed to self-fold and form a stem-handle-loop structure, which comprises a 5' single-stranded handle comprising the promoter portion (P), a double-stranded stem comprising the pair of self-folding segments (i.e., A and Ac) hybridized to each other, and a single-stranded loop comprising the sequence between the pair of self-folding segments. In a fifth step (5), the 3' end of the handle-stem-loop structure is extended to generate a double-stranded promoter comprising the promoter portion (P) and its complementary sequence (Pc) hybridized to each other. In a sixth step (6), transcription is initiated from the double-stranded promoter to generate multiple copies of a single-stranded RNA product (+) comprising the target polynucleotide sequence (T) and the complementary sequence of the promoter portion (Pc), wherein the complementary sequence of the promoter portion (Pc) is at the 3' end of the single-stranded RNA product. In a seventh step (7), the single-stranded RNA product is hybridized with the composite primer. In an eighth step (8), the 3' end of the composite primer is extended to generate a RNA/DNA hybrid. In a ninth step (9), the RNA portion is removed from the RNA/DNA hybrid to generate the single-stranded DNA template. Steps (4), (5) and (6) are continued in order to exponentially generate multiple copies of the single-stranded RNA product. The single-stranded RNA product can be detected using, for example, a molecular beacon comprising a sequence complementary to a portion of the target polynucleotide sequence, wherein said sequence is not found in the composite primer or the 5' end portion of the target polynucleotide sequence, or their respective complementary sequences.

The use of a composite primer or a template switching oligonucleotide that comprising a universal portion (U) provides a very simple system for multiplex nucleic acid detection, such as in multiplex sexually transmitted diseases detection and blood bank screen for viruses. For example, a single primer containing a universal portion can be used in blood bank multiplex amplification of HIV, HCV, and HBV.

Optionally, the methods of the invention further comprises a detection step that detects the generation of the single-stranded RNA product. In one aspect, the detection step comprises hybridizing a detection means such as a molecular beacon comprising a target-recognition portion which is located between the 3' and 5' ends of the target polynucleotide sequence.

While FIGS. 1-7 illustrate the amplification of a positive (+)-sense target polynucleotide sequence, by using a negative (−)-sense composite primer, the same steps can be followed to amplify a negative (−)-sense target polynucleotide sequence, by using a positive (+)-sense composite primer.

The methods of the invention can also be used for the selective amplification and detection of more than one target polynucleotide sequences. FIG. 8 provides the generic sequence formula of a composite primer, a blocking sequence, a RNA/DNA hybrid, and a detection means for multiple RNA target polynucleotide sequences using the methods of the invention.

5.2 Kits and Amplification Reaction Mixtures

The invention also relates to kits useful for the selective amplification, and optionally, the detection, of one or more target polynucleotide sequences, as well as compositions comprising one or more target polynucleotide sequence, one or more composite primer, and one or more amplification reaction product.

In certain embodiments, the kit comprises, for each target polynucleotide sequence, at least one composite primer comprising (i) a 5' promoter portion, and (ii) a 3' target-recognition portion which is complementary to the 3' end portion of a target polynucleotide sequence, and optionally a means for identifying the 5' end of the target polynucleotide sequence, and optionally a detection means.

In certain embodiments, the composite primer(s), the optional identifying means, and optional the detection means are placed in the same container means of the kit. In certain embodiments, the composite primer(s), the optional identifying means, and the optional detection means are placed in separate container means of the kit.

Optionally, the kits of the invention further comprises an instruction manual describing, for example, the component(s) within each container means, the order of using the one or more container means, etc.

In certain embodiments, the composition comprises the composite primer(s) described above and an amplification reaction product such as a handle-stem-loop structure or a stem-loop structure. The handle-stem-loop structure comprises a (i) a 5' single-stranded handle comprising a promoter portion (P), (ii) a double-stranded stem comprising at least one pair of self-folding segments hybridized to each other, wherein one of the self-folding segment is a 5' end portion of the target polynucleotide sequence or its complementary sequence, and (iii) a single-stranded loop comprising the sequence between the pair of self-folding segments. The stem-loop structure differs from the handle-stem-loop structure in that the 5' single-stranded handle has become double-stranded following primer extension.

6. EXAMPLES

Examples are provided below illustrating certain aspects and embodiments of the invention. The examples below are believed to accurately reflect the details of experiments actually performed, however, it is possible that some minor discrepancies may exist between the work actually performed and the experimental details set forth below which do not affect the conclusions of these experiments or the ability of skilled artisans to practice them. Skilled artisans will appreciate that these examples are not intended to limit the invention to the specific embodiments described therein. Additionally, those skilled in the art, using the techniques, materials and methods described herein, could easily devise and optimize alternative amplification systems for carrying out these and related methods while still being within the spirit and scope of the present invention.

6.1 Example 1

Target-Specific Amplification with the Method of the Invention

The following experiment was conducted to evaluate isothermal amplification with a composite primer of the invention. HCV RNA was amplified using a method of the invention.

6.1.1 Materials and Methods
I. Oligonucleotides
1. Composite Primer
The composite primer had the following sequence and was used at 10 pmol/rxn:

```
                                           (SEQ ID NO: 1)
5' AATTT AATAC GACTC ACTAT AGGGA GACTA GCCAT

GGGCA ATTCC GGTGT ACTCA 3'.
```

The nucleotides at position 1 to 27 constitute the T7 promoter sequence; the underlined section is the folding sequence; and the rest of the 3' sequence is complementary to a portion of HCV RNA.

2. Detection Probe
The detection probe (a molecular beacon) had the following sequence and was used at 5 pmol/rxn:

```
                                           (SEQ ID NO: 2)
5' Fam-CGUUC CGCAG ACCAC UAUGA ACG-Dabcyl 3'.
```

The nucleotides at position of 5 to 19 is complementary to a portion of an HCV RNA and can hybridize to the amplified product.

3. Blocking Sequence
The blocking sequence had the following sequence and was used at 2.5 pmol/rxn:

```
                                           (SEQ ID NO: 3)
5' AUGGC UAGAC GCUUU CUGCG UGAAG 3'
```

II. Reagents
1. Amplification Buffer
The "amplification buffer" comprised 26 mM Trizma base (pH 8.0), 25 mM $MgCl_2$, 23.3 mM $KCl_2$, 3.33% (v/v) glycerol, 0.05 mM zinc acetate, 0.76 mM dATP, 0.76 mM dCTP, 0.76 mM dGTP, 0.76 mM dTTP, 6.0 mM ATP, 6.0 mM CTP, 6.0 mM GTP, and 6.0 mM UTP, pH 7.81 to 8.0 at 22° C.

2. Enzyme Mixture
The "enzyme mixture" comprised 70 mM N-acetyl-L-cysteine, 10% (v/v) TRITON X-102, 16 mM HEPES, 1 mM EDTA, 20 mM Trizma base buffer, 50 mM $KCl_2$, 20% (v/v) glycerol, 165.6 mM trehalose, pH 7, and containing 224 RTU/µL Moloney murine leukemia virus ("MMLV") reverse transcriptase and 140 U/µL T7 RNA polymerase.

III. Machine
The Mx3005P™ Real-Time PCR System (Strategene, La Jolla, Calif.) was used as the detection machine.

IV. Detail Protocol
The experiment was performed using the following steps:
Step (1): Added 75 µl of amplification buffer containing 10 pmol composite primer, 2.5 pmol blocking oligonucleotide, 5 pmol detection probe, and 3 µl of HCV RNA-containing buffer to each well of a 96-well microtiter plate. 3 µl of buffer without HCV RNA target were added as negative control. Covered the plate with a clear sealing card.
Step (2): Incubated the 96-well microtiter plate at 60° C. for 0 to 5 minutes.
Step (3): Incubated the 96-well microtiter plate at 42° C. for 2 to 5 minutes.
Step (4): Added 25 µl of enzyme mixture to each well.
Step (5): Immediately placed the plate into Mx3005P™ Real-Time PCR System (isothermal incubation at 42° C.) and measured fluorescence of each well every 1 minute. Ct values, which served as indicators of the amount of the amplicon synthesized, were determined from the monitored fluorescent signals.

6.1.2 Results

As can be seen in FIG. 9, when 0.1 pg of HCV RNA transcripts was added into the reaction, the Dt value was about 26 minutes (see line with closed circles: —●—), while no detectable signal above background was observed in the negative control (no HCV RNA was added) (see line with closed squares: —■—). Dt is the time required for the fluorescent signal to cross the threshold (i.e., exceed background level).

6.2 Example 2

Effect of Different Length of Folding Sequences in the Method of the Invention

The following experiment studied the effect of different length of folding sequence in the composite primer in a method of the invention.

6.2.1 Materials and Methods

The composite primer had one of the following sequence:

```
5' AATTT AATAC GACTC ACTAT AGGGA GACTA GCCAT
GGGCA ATTCC GGTGT ACTCA 3'
(SEQ ID NO: 1, with a folding sequence of 9
bases), 5' AATTT AATAC GACTC ACTAT AGGGA GACTA GCCAT
GGCCG GCAAT TCCGG TGTAC TCA 3'
(SEQ ID NO: 4, with a folding sequence of
12 bases),
or 5' AATTT AATAC GACTC ACTAT AGGGA GACTA GCCAT
GGCGT TAGGC AATTC CGGTG TACTC A 3'
(SEQ ID NO: 5, with a folding sequence of
15 bases).
```

The nucleotides at position 1 to 27 constitute the T7 promoter sequence; the underlined section is the folding sequence; and the rest of the 3' sequence is complementary to a portion of HCV RNA.

Except that the HCV target was used at 10 pg per reaction, the detection probe, blocking sequence, reagents, machine, and experimental protocol were essentially the same as those described in Example 1.

6.2.2 Results

As shown in FIG. 10, the Dt value for the three different composite primers was similar (about 12 minutes). Line A plots the Dt value for the composite primer comprising the amino acid sequence of SEQ ID NO:1. Line B plots the Dt value for the composite primer comprising the amino acid sequence of SEQ ID NO:4. Line C plots the Dt value for the composite primer comprising the amino acid sequence of SEQ ID NO:5.

In another experiment (data not shown), the following composite primer with a long folding sequence (see below) was used, and no detectable signal above background were observed:

```
5' AATTT AATAC GACTC ACTAT AGGGA GACTA GCCAT
GGCGT TAGTA TGAGG GCAAT TCCGG TGTAC TCA 3'
(SEQ ID NO: 6, with a folding sequence of 22
bases, see underlined).
```

These results indicate that the length of the folding sequence could affect the amplification efficacy.

6.3 Example 3

Quantitative Detection of Target Nucleic Acid Using the Method of the Invention

The following experiment demonstrates that the methods of the invention can be used to perform quantitative detection of target nucleic acid, using HCV RNA transcripts as an example.

6.3.1 Materials and Methods

The composite primer had the following sequence:

```
5' AATTT AATAC GACTC ACTAT AGGGA GACTA GCCAT
GGCGG GCAAT TCCGG TGTAC TCA 3'
(SEQ ID NO: 4, with a folding sequence of 12
bases, see underlined).
```

Except that the HCV target was used at 10 pg/reaction in this example, the detection probe, blocking sequence, reagents, machine, and experimental protocol were essentially the same as those described in Example 1.

6.3.2 Results

As shown in FIG. 11, when 10 pg, 1 pg or 0.1 pg of HCV RNA transcripts were added into the reaction, the Dt value was about 14 minutes (see line with closed circles: —●—), 20 minutes (see line with closed squares: —■—) or 28 minutes (see line with closed triangles: —▲—), respectively, while no detectable signal above background was observed in the negative control (no HCV RNA was added).

These results indicate that the methods of the invention can be used for quantitative detection of target nucleic acid.

7. SPECIFIC ASPECTS/EMBODIMENTS, CITATION OF REFERENCES

The present invention is not to be limited in scope by the specific aspects and embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

What is claimed is:

1. A method for selective amplification of a target polynucleotide sequence (T), comprising the steps of:
   (a) hybridizing the target polynucleotide sequence (+) with a first composite primer (−), said first composite primer comprising a 5' promoter portion (P) and a 3' target-recognition portion which is complementary to the 3' end portion of the target polynucleotide sequence, wherein the first composite primer comprises a first self-folding segment between the promoter portion and the 3' target recognition region;
   (b) identifying the 5' end portion of the target polynucleotide sequence;
   (c) extending the 3' end of the first composite primer and generating a first single-stranded DNA template (−) comprising the promoter portion (P) and the complementary sequence of the target polynucleotide sequence (Tc), said first single-stranded DNA template comprising the first self-folding segment and a second self-folding segment that is complementary to the first self-folding segment, wherein the promoter portion (P) is at the 5' end of the first single-stranded DNA template and the second self-folding segments is at the 3' end of the first single-stranded DNA template;
   (d) allowing the first single-stranded DNA template to self-fold and form a first handle-stem-loop structure, which comprises a 5' single-stranded handle comprising the promoter portion (P) and a double-stranded stem comprising the first and second self-folding segments hybridized to each other;
   (e) extending the 3' end of the first handle-stem-loop structure to generate a double-stranded promoter comprising the promoter portion (P) and its complementary sequence (Pc) hybridized to each other; and
   (f) initiating transcription from the double-stranded promoter to generate multiple copies of a single-stranded RNA product (+) comprising the target polynucleotide sequence (T).

2. The method of claim 1, wherein the target polynucleotide sequence is RNA.

3. The method of claim 2, wherein step (c) comprises extending the 3' end of the first composite primer to generate a first RNA/DNA hybrid and removing the RNA portion of the first RNA/DNA hybrid to generate the first single-stranded DNA template.

4. The method of claim 3, wherein the target polynucleotide sequence is within a longer polynucleotide template, and wherein step (b) comprises identifying the 5' end of the target polynucleotide sequence by using an enzyme to cleave at a region of the polynucleotide template immediately upstream of the 5' end of the target polynucleotide sequence.

5. The method of claim 3, wherein the target polynucleotide sequence is within a longer polynucleotide template, and wherein step (b) comprises identifying the 5' end of the target polynucleotide sequence by hybridizing a blocking oligonucleotide (−) to a region of the polynucleotide template immediately upstream of the 5' end of the target polynucleotide sequence, wherein said blocking oligonucleotide block extension of the first composite primer in step (c).

6. The method of claim 5, wherein the first composite primer further comprises, between the promoter portion (P) and the 3' target-recognition portion, a segment corresponding to the 5' end portion of the target polynucleotide sequence, wherein this segment and its complementary sequence form said first pair of self-folding segments, the method further comprising the following steps after step (f):
   (g) hybridizing the single-stranded RNA product (+) with the first composite primer (−) and extending the 3' end of the first composite primer to generate a second RNA/DNA hybrid;
   (h) removing the RNA portion of the second RNA/DNA hybrid to generate the first single-stranded DNA template (−); and
   continuing steps (d), (e) and (f).

7. The method of claim 5, wherein the 3' target-recognition portion of the first composite primer comprises a segment corresponding to the 5' end portion of the target polynucleotide sequence, wherein this segment and its complementary sequence form said first pair of self-folding segments, the method further comprising the following steps after step (f):
   (g) hybridizing the single-stranded RNA product (+) with the first composite primer (−) and extending the 3' end of the first composite primer to generate a second RNA/DNA hybrid;
   (h) removing the RNA portion of the second RNA/DNA hybrid to generate a second single-stranded DNA template (−) comprising the promoter portion (P) and the complementary sequence of the target polynucleotide sequence (Tc), said second single-stranded DNA template comprising a second pair of self-folding segments that are complementary to each other, wherein the promoter portion (P) is at the 5' end of the second single-stranded DNA template and one of the second pair of self-folding segments is at the 3' end of the second single-stranded DNA template;
   (i) allowing the second single-stranded DNA template to self-fold and form a second handle-stem-loop structure, which comprises a 5' single-stranded handle comprising the promoter portion (P) and a double-stranded stem comprising the second pair of self-folding segments hybridized to each other;
   (j) extending the 3' end of the second handle-stem-loop structure to generate a double-stranded promoter comprising the promoter portion (P) and its complementary sequence (Pc) hybridized to each other; and
   (k) initiating transcription from the double-stranded promoter to generate multiple copies of the single-stranded RNA product (+).

8. The method of claim 5, wherein said first pair of self-folding segments comprise a segment corresponding to the 5' end portion of the target polynucleotide sequence and its complementary sequence located at a separate portion of the target polynucleotide sequence, the method further comprising the following steps after step (f):
   (g) hybridizing the single-stranded RNA product (+) with the first composite primer (−) and extending the 3' end of the first composite primer to generate a second RNA/DNA hybrid;
   (h) removing the RNA portion of the second RNA/DNA hybrid to generate a second single-stranded DNA template (−) comprising the promoter portion (P) and the complementary sequence of the target polynucleotide sequence (Tc), said second single-stranded DNA template comprising a second pair of self-folding segments that are complementary to each other, wherein the promoter portion (P) is at the 5' end of the second single-stranded DNA template and one of the second pair of self-folding segments is at the 3' end of the second single-stranded DNA template;
   (i) allowing the second single-stranded DNA template to self-fold and form a second handle-stem-loop structure, which comprises a 5' single-stranded handle comprising the promoter portion (P) and a double-stranded stem comprising the second pair of self-folding segments hybridized to each other;

(j) extending the 3' end of the second handle-stem-loop structure to generate a double-stranded promoter comprising the promoter portion (P) and its complementary sequence (Pc) hybridized to each other; and (k) initiating transcription from the double-stranded promoter to generate multiple copies of the single-stranded RNA product (+).

9. The method of claim 3, wherein the target polynucleotide sequence is within a longer polynucleotide template, and wherein step (b) comprises identifying the 5' end of the target polynucleotide sequence by hybridizing a template switching oligonucleotide (TSO) (−) to a region of the polynucleotide template immediately upstream of the 5' end of the target polynucleotide sequence, and wherein step (c) comprises extending the 3' end of the first composite primer over a portion of said template switching oligonucleotide (TSO).

10. The method of claim 9, wherein the first composite primer further comprises, from 5' to 3' and between the promoter portion (P) and the 3' target-recognition portion, a universal portion (U) that is not present in the target polynucleotide sequence or its complementary sequence, and the template switching oligonucleotide (TSO) comprising, from 5' to 3', the universal portion (U) and a portion complementary to the region of the polynucleotide template immediately upstream of the 5' end of the target polynucleotide sequence, wherein the first pair of self-folding segments comprise the universal portion (U) and its complementary sequence, the method further comprising the following steps after step (f):

(g) hybridizing the single-stranded RNA product (+) with the first composite primer or a second composite primer (−) and extending the 3' end of the second composite primer to generate a second RNA/DNA hybrid, wherein the second composite primer comprises the 5' promoter portion (P) and the universal portion (U);

(h) removing the RNA portion of the second RNA/DNA hybrid to generate the first single-stranded DNA template (−); and continuing steps (d), (e) and (f).

11. The method of claim 1, wherein the target polynucleotide sequence is DNA.

12. The method of claim 11, comprising a denaturing step before step (a).

13. The method of claim 12, wherein the target polynucleotide sequence is within a longer polynucleotide template, and wherein step (b) comprises identifying the 5' end of the target polynucleotide sequence by using an enzyme to cleave at a region of the polynucleotide template immediately upstream of the 5' end of the target polynucleotide sequence.

14. The method of claim 12, wherein the target polynucleotide sequence is within a longer polynucleotide template, and wherein step (b) comprises identifying the 5' end of the target polynucleotide sequence by hybridizing a blocking oligonucleotide (−) to a region of the polynucleotide template immediately upstream of the 5' end of the target polynucleotide sequence, wherein said blocking oligonucleotide block extension of the first composite primer in step (c).

15. The method of claim 14, wherein the first composite primer further comprises, between the promoter portion (P) and the 3' target-recognition portion, a segment corresponding to the 5' end portion of the target polynucleotide sequence, wherein this segment and its complementary sequence form said first pair of self-folding segments, the method further comprising the following steps after step (f):

(g) hybridizing the single-stranded RNA product (+) with the first composite primer (−) and extending the 3' end of the first composite primer to generate a RNA/DNA hybrid;

(h) removing the RNA portion of the RNA/DNA hybrid to generate the first single-stranded DNA template (−); and continuing steps (d), (e) and (f).

16. The method of claim 14, wherein the 3' target-recognition portion of the first composite primer comprises a segment corresponding to the 5' end portion of the target polynucleotide sequence, wherein this segment and its complementary sequence form said first pair of self-folding segments, the method further comprising the following steps after step (f):

(g) hybridizing the single-stranded RNA product (+) with the first composite primer (−) and extending the 3' end of the first composite primer to generate a RNA/DNA hybrid;

(h) removing the RNA portion of the RNA/DNA hybrid to generate a second single-stranded DNA template (−) comprising the promoter portion (P) and the complementary sequence of the target polynucleotide sequence (Tc), said second single-stranded DNA template comprising a second pair of self-folding segments that are complementary to each other, wherein the promoter portion (P) is at the 5' end of the second single-stranded DNA template and one of the second pair of self-folding segments is at the 3' end of the second single-stranded DNA template;

(i) allowing the second single-stranded DNA template to self-fold and form a second handle-stem-loop structure, which comprises a 5' single-stranded handle comprising the promoter portion (P) and a double-stranded stem comprising the second pair of self-folding segments hybridized to each other;

(j) extending the 3' end of the second handle-stem-loop structure to generate a double-stranded promoter comprising the promoter portion (P) and its complementary sequence (Pc) hybridized to each other; and (k) initiating transcription from the double-stranded promoter to generate multiple copies of the single-stranded RNA product (+).

17. The method of claim 14, wherein said first pair of self-folding segments comprise a segment corresponding to the 5' end portion of the target polynucleotide sequence and its complementary sequence located at a separate portion of the target polynucleotide sequence, the method further comprising the following steps after step (f):

(g) hybridizing the single-stranded RNA product (+) with the first composite primer (−) and extending the 3' end of the first composite primer to generate a RNA/DNA hybrid;

(h) removing the RNA portion of the RNA/DNA hybrid to generate a second single-stranded DNA template (−) comprising the promoter portion (P) and the complementary sequence of the target polynucleotide sequence (Tc), said second single-stranded DNA template comprising a second pair of self-folding segments that are complementary to each other, wherein the promoter portion (P) is at the 5' end of the second single-stranded DNA template and one of the second pair of self-folding segments is at the 3' end of the second single-stranded DNA template;

(i) allowing the second single-stranded DNA template to self-fold and form a second handle-stem-loop structure, which comprises a 5' single-stranded handle comprising the promoter portion (P) and a double-stranded stem comprising the second pair of self-folding segments hybridized to each other;

(j) extending the 3' end of the second handle-stem-loop structure to generate a double-stranded promoter comprising the promoter portion (P) and its complementary sequence (Pc) hybridized to each other; and (k) initiating transcription from the double-stranded promoter to generate multiple copies of the single-stranded RNA product (+).

18. The method of claim 12, wherein the target polynucleotide sequence is within a longer polynucleotide template, and wherein step (b) comprises identifying the 5' end of the target polynucleotide sequence by hybridizing a template switching oligonucleotide (TSO) (-) to a region of the polynucleotide template immediately upstream of the 5' end of the target polynucleotide sequence, and wherein step (c) comprises extending the 3' end of the first composite primer over a portion of said template switching oligonucleotide (TSO).

19. The method of claim 18, wherein the first composite primer further comprises, from 5' to 3' and between the promoter portion (P) and the 3' target-recognition portion, a universal portion (U) that is not present in the target polynucleotide sequence or its complementary sequence, and the template switching oligonucleotide (TSO) comprising, from 5' to 3', the universal portion (U) and a portion complementary to the region of the polynucleotide template immediately upstream of the 5' end of the target polynucleotide sequence, wherein the first pair of self-folding segments comprise the universal portion (U) and its complementary sequence, the method further comprising the following steps after step (f):

(g) hybridizing the single-stranded RNA product (+) with the first composite primer or a second composite primer (-) and extending the 3' end of the second composite primer to generate a second RNA/DNA hybrid, wherein the second composite primer comprises the 5' promoter portion (P) and the universal portion (U);

(h) removing the RNA portion of the second RNA/DNA hybrid to generate the first single-stranded DNA template (-); and continuing steps (d), (e) and (f).

20. The method of claim 1, wherein the first composite primer further comprises, from 5' to 3' and between the promoter portion (P) and the 3' target-recognition portion, a universal portion (U) that is not present in the target polynucleotide sequence or its complementary sequence, and a segment corresponding to the 5' end portion of the target polynucleotide sequence, wherein this segment and its complementary sequence form said first pair of self-folding segments, the method further comprising the following steps after step (f):

(g) hybridizing the single-stranded RNA product (+) with the first composite primer or a second composite primer (-) and extending the 3' end of the second composite primer to generate a second RNA/DNA hybrid, wherein the second composite primer comprises the 5' promoter portion (P) and the universal portion (U);

(h) removing the RNA portion of the second RNA/DNA hybrid to generate a second single-stranded DNA template (-) comprising the promoter portion (P), the universal portion (U), and the complementary sequence of the target polynucleotide sequence (Tc), said second single-stranded DNA template comprises a second pair of self-folding segments that are complementary to and separated from each other, wherein the promoter portion (P) is at the 5' end of the second single-stranded DNA template and one of the second pair of self-folding segments is at the 3' end of the second single-stranded DNA template;

(i) allowing the second single-stranded DNA template to self-fold and form a second handle-stem-loop structure which comprises a 5' single-stranded handle comprising the promoter portion (P), a double-stranded stem comprising the second pair of self-folding segments hybridized to each other, and a single-stranded loop comprising the sequence between the second pair of self-folding segments;

(j) extending the 3' end of the second handle-stem-loop structure to generate a double-stranded promoter comprising the promoter portion (P) and its complementary sequence (Pc) hybridized to each other; and (k) initiating transcription from the double-stranded promoter to generate multiple copies of the single-stranded RNA product (+).

* * * * *

SEQUENCE LISTING

<160> NUMBER OF SEQ ID NOS: 6

<210> SEQ ID NO 1
<211> LENGTH: 55
<212> TYPE: DNA

```
<213> ORGANISM: Artificial Sequence
<220> FEATURE:
<223> OTHER INFORMATION: composite primer(with a folding sequence of 9
      bases)

<400> SEQUENCE: 1
aatttaatac gactcactat agggagacta gccatgggca attccggtgt actca          55

<210> SEQ ID NO 2
<211> LENGTH: 23
<212> TYPE: RNA
<213> ORGANISM: Artificial Sequence
<220> FEATURE:
<223> OTHER INFORMATION: detection probe

<400> SEQUENCE: 2
cguuccgcag accacuauga acg                                            23

<210> SEQ ID NO 3
<211> LENGTH: 25
<212> TYPE: RNA
<213> ORGANISM: Artificial Sequence
<220> FEATURE:
<223> OTHER INFORMATION: blocking sequence

<400> SEQUENCE: 3
auggcuagac gcuuucugcg ugaag                                          25

<210> SEQ ID NO 4
<211> LENGTH: 58
<212> TYPE: DNA
<213> ORGANISM: Artificial Sequence
<220> FEATURE:
<223> OTHER INFORMATION: composite primer(with a folding sequence of 12
      bases)

<400> SEQUENCE: 4
aatttaatac gactcactat agggagacta gccatggccg gcaattccgg tgtactca      58

<210> SEQ ID NO 5
<211> LENGTH: 61
<212> TYPE: DNA
<213> ORGANISM: Artificial Sequence
<220> FEATURE:
<223> OTHER INFORMATION: composite primer(with a folding sequence of 15
      bases)

<400> SEQUENCE: 5
aatttaatac gactcactat agggagacta gccatggcgt taggcaattc cggtgtactc    60
a                                                                    61

<210> SEQ ID NO 6
<211> LENGTH: 68
<212> TYPE: DNA
<213> ORGANISM: Artificial Sequence
<220> FEATURE:
<223> OTHER INFORMATION: composite primer(with a folding sequence of 22
      bases)

<400> SEQUENCE: 6
aatttaatac gactcactat agggagacta gccatggcgt tagtatgagg gcaattccgg    60
tgtactca                                                             68

1
```